United States Patent
Yamaji et al.

(10) Patent No.: US 6,716,613 B1
(45) Date of Patent: Apr. 6, 2004

(54) METALLOPROTEASE HAVING AGGRECANASE ACTIVITY

(75) Inventors: Noboru Yamaji, Ibaraki (JP); Kouichi Nishimura, Ibaraki (JP); Kunitake Abe, Ibaraki (JP); Osamu Ohara, Chiba (JP); Takahiro Nagase, Chiba (JP); Nobuo Nomura, Chiba (JP)

(73) Assignees: Yamanouchi Pharmaceutical Co., Ltd., Tokyo (JP); Kazusa DNA Research Institute, Chiba (JP)

( * ) Notice: Subject to any disclaimer, the term of this patent is extended or adjusted under 35 U.S.C. 154(b) by 44 days.

(21) Appl. No.: 10/009,332

(22) PCT Filed: Nov. 10, 2000

(86) PCT No.: PCT/JP00/07917

§ 371 (c)(1),
(2), (4) Date: Dec. 10, 2001

(87) PCT Pub. No.: WO01/34785

PCT Pub. Date: May 17, 2001

(30) Foreign Application Priority Data

Nov. 11, 1999 (JP) .............................. 11/321740
May 16, 2000 (JP) ....................... 2000-144020

(51) Int. Cl.[7] .................. C12N 9/48; C12N 15/00; C12N 1/20; C12P 21/04; C07H 21/04
(52) U.S. Cl. ................. 435/212; 435/252.3; 435/320.1; 435/71.1; 536/23.2
(58) Field of Search ............................ 435/212, 252.3, 435/320.1, 71.1, 440; 536/23.2

(56) References Cited

U.S. PATENT DOCUMENTS

2002/0115842 A1 * 8/2002 Friddle et al. ............. 536/23.2

OTHER PUBLICATIONS

Kuno et al. Molecular cloning of a gene encoding a new type of metalloproteinase–disintegrin family protein with thrombospondin motifs as an inflammation associated gene. J. of Biol. Chem. vol. 272, No. 1, pp. 556–562, 1997.*

International Search Report.

Flannery, Carl R., et al "Expression of ADAMTS Homologues in Articular Cartilage", Biochemical and Biophysical Research Communications vol. 260, pp. 318–322, Jul. 1999.

Abbaszade, Ilgar et al., "Cloning and Characterization of ADAMTS11, and Aggrecanase from the ADAMTS Family" The Journal of Biological Chemistry, vol. 274, No. 33, pp. 23443–23450, 1999.

Tortorella, M.D. et al "Purification and Cloning of Aggrecanase–1: A Member of the ADAMTS Family of Proteins", Science, vol. 284, pp. 1664–1666, Jun. 4, 1999.

* cited by examiner

Primary Examiner—P. Achutamurthy
Assistant Examiner—Yong D Pak
(74) Attorney, Agent, or Firm—Sughrue Mion, PLLC

(57) ABSTRACT

This invention provides a novel metalloprotease having an aggrecanase activity which causes joint diseases, a gene coding for this metalloprotease, a promoter of the above metalloprotease, a method for screening a drug with the use of the above metalloprotease and a pharmaceutical composition for inhibiting degradation of proteoglycans, which comprises as the active ingredient a substance capable of inhibiting the aggrecanase activity of the above metalloprotease.

10 Claims, 8 Drawing Sheets

IL-1 TREATMENT (TIME)

SEQUENCE LISTING

```
<160> NUMBER OF SEQ ID NOS: 35

<210> SEQ ID NO 1
<211> LENGTH: 950
<212> TYPE: PRT
<213> ORGANISM: Homo sapiens

<400> SEQUENCE: 1

Met Leu Leu Leu Gly Ile Leu Thr Leu Ala Phe Ala Gly Arg Thr Ala
1               5                   10                  15

Gly Gly Phe Glu Pro Glu Arg Glu Val Val Pro Ile Arg Leu Asp
            20                  25                  30

Pro Asp Ile Asn Gly Arg Arg Tyr Tyr Trp Arg Gly Pro Glu Asp Ser
            35                  40                  45

Gly Asp Gln Gly Leu Ile Phe Gln Ile Thr Ala Phe Gln Glu Asp Phe
    50                  55                  60

Tyr Leu His Leu Thr Pro Asp Ala Gln Phe Leu Ala Pro Ala Phe Ser
65                  70                  75                  80

Thr Glu His Leu Gly Val Pro Leu Gln Gly Leu Thr Gly Gly Ser Ser
                85                  90                  95

Asp Leu Arg Arg Cys Phe Tyr Ser Gly Asp Val Asn Ala Glu Pro Asp
            100                 105                 110

Ser Phe Ala Ala Val Ser Leu Cys Gly Gly Leu Arg Gly Ala Phe Gly
            115                 120                 125

Tyr Arg Gly Ala Glu Tyr Val Ile Ser Pro Leu Pro Asn Ala Ser Ala
        130                 135                 140

Pro Ala Ala Gln Arg Asn Ser Gln Gly Ala His Leu Leu Gln Arg Arg
```

-continued

```
145                 150                 155                 160
Gly Val Pro Gly Gly Pro Ser Gly Asp Pro Thr Ser Arg Cys Gly Val
                165                 170                 175
Ala Ser Gly Trp Asn Pro Ala Ile Leu Arg Ala Leu Asp Pro Tyr Lys
            180                 185                 190
Pro Arg Arg Ala Gly Phe Gly Glu Ser Arg Ser Arg Arg Ser Gly
        195                 200                 205
Arg Ala Lys Arg Phe Val Ser Ile Pro Arg Tyr Val Glu Thr Leu Val
    210                 215                 220
Val Ala Asp Glu Ser Met Val Lys Phe His Gly Ala Asp Leu Glu His
225                 230                 235                 240
Tyr Leu Leu Thr Leu Leu Ala Thr Ala Ala Arg Leu Tyr Arg His Pro
                245                 250                 255
Ser Ile Leu Asn Pro Ile Asn Ile Val Val Lys Val Leu Leu Leu
                260                 265                 270
Arg Asp Arg Asp Ser Gly Pro Lys Val Thr Gly Asn Ala Ala Leu Thr
            275                 280                 285
Leu Arg Asn Phe Cys Ala Trp Gln Lys Lys Leu Asn Lys Val Ser Asp
    290                 295                 300
Lys His Pro Glu Tyr Trp Asp Thr Ala Ile Leu Phe Thr Arg Gln Asp
305                 310                 315                 320
Leu Cys Gly Ala Thr Thr Cys Asp Thr Leu Gly Met Ala Asp Val Gly
                325                 330                 335
Thr Met Cys Asp Pro Lys Arg Ser Cys Ser Val Ile Glu Asp Asp Gly
                340                 345                 350
Leu Pro Ser Ala Phe Thr Thr Ala His Glu Leu Gly His Val Phe Asn
            355                 360                 365
Met Pro His Asp Asn Val Lys Val Cys Glu Glu Val Phe Gly Lys Leu
    370                 375                 380
Arg Ala Asn His Met Met Ser Pro Thr Leu Ile Gln Ile Asp Arg Ala
385                 390                 395                 400
Asn Pro Trp Ser Ala Cys Ser Ala Ala Ile Ile Thr Asp Phe Leu Asp
                405                 410                 415
Ser Gly His Gly Asp Cys Leu Leu Asp Gln Pro Ser Lys Pro Ile Ser
            420                 425                 430
Leu Pro Glu Asp Leu Pro Gly Ala Ser Tyr Thr Leu Ser Gln Gln Cys
    435                 440                 445
Glu Leu Ala Phe Gly Val Gly Ser Lys Pro Cys Pro Tyr Met Gln Tyr
    450                 455                 460
Cys Thr Lys Leu Trp Cys Thr Gly Lys Ala Lys Gly Gln Met Val Cys
465                 470                 475                 480
Gln Thr Arg His Phe Pro Trp Ala Asp Gly Thr Ser Cys Gly Glu Gly
                485                 490                 495
Lys Leu Cys Leu Lys Gly Ala Cys Val Glu Arg His Asn Leu Asn Lys
            500                 505                 510
His Arg Val Asp Gly Ser Trp Ala Lys Trp Asp Pro Tyr Gly Pro Cys
    515                 520                 525
Ser Arg Thr Cys Gly Gly Gly Val Gln Leu Ala Arg Arg Gln Cys Thr
    530                 535                 540
Asn Pro Thr Pro Ala Asn Gly Gly Lys Tyr Cys Glu Gly Val Arg Val
545                 550                 555                 560
Lys Tyr Arg Ser Cys Asn Leu Glu Pro Cys Pro Ser Ser Ala Ser Gly
                565                 570                 575
```

-continued

```
Lys Ser Phe Arg Glu Glu Gln Cys Glu Ala Phe Asn Gly Tyr Asn His
                580                 585                 590

Ser Thr Asn Arg Leu Thr Leu Ala Val Ala Trp Val Pro Lys Tyr Ser
            595                 600                 605

Gly Val Ser Pro Arg Asp Lys Cys Lys Leu Ile Cys Arg Ala Asn Gly
        610                 615                 620

Thr Gly Tyr Phe Tyr Val Leu Ala Pro Lys Val Val Asp Gly Thr Leu
625                 630                 635                 640

Cys Ser Pro Asp Ser Thr Ser Val Cys Val Gln Gly Lys Cys Ile Lys
                645                 650                 655

Ala Gly Cys Asp Gly Asn Leu Gly Ser Lys Lys Arg Phe Asp Lys Cys
            660                 665                 670

Gly Val Cys Gly Gly Asp Asn Lys Ser Cys Lys Lys Val Thr Gly Leu
        675                 680                 685

Phe Thr Lys Pro Met His Gly Tyr Asn Phe Val Val Ala Ile Pro Ala
690                 695                 700

Gly Ala Ser Ser Ile Asp Ile Arg Gln Arg Gly Tyr Lys Gly Leu Ile
705                 710                 715                 720

Gly Asp Asp Asn Tyr Leu Ala Leu Lys Asn Ser Gln Gly Lys Tyr Leu
                725                 730                 735

Leu Asn Gly His Phe Val Val Ser Ala Val Glu Arg Asp Leu Val Val
            740                 745                 750

Lys Gly Ser Leu Leu Arg Tyr Ser Gly Thr Gly Thr Ala Val Glu Ser
        755                 760                 765

Leu Gln Ala Ser Arg Pro Ile Leu Glu Pro Leu Thr Val Glu Val Leu
770                 775                 780

Ser Val Gly Lys Met Thr Pro Pro Arg Val Arg Tyr Ser Phe Tyr Leu
785                 790                 795                 800

Pro Lys Glu Pro Arg Glu Asp Lys Ser Ser His Pro Lys Asp Pro Arg
                805                 810                 815

Gly Pro Ser Val Leu His Asn Ser Val Leu Ser Leu Ser Asn Gln Val
            820                 825                 830

Glu Gln Pro Asp Asp Arg Pro Pro Ala Arg Trp Val Ala Gly Ser Trp
        835                 840                 845

Gly Pro Cys Ser Ala Ser Cys Gly Ser Gly Leu Gln Lys Arg Ala Val
850                 855                 860

Asp Cys Arg Gly Ser Ala Gly Gln Arg Thr Val Pro Ala Cys Asp Ala
865                 870                 875                 880

Ala His Arg Pro Val Glu Thr Gln Ala Cys Gly Glu Pro Cys Pro Thr
                885                 890                 895

Trp Glu Leu Ser Ala Trp Ser Pro Cys Ser Lys Ser Cys Gly Arg Gly
            900                 905                 910

Phe Gln Arg Arg Ser Leu Lys Cys Val Gly His Gly Gly Arg Leu Leu
        915                 920                 925

Ala Arg Asp Gln Cys Asn Leu His Arg Lys Pro Gln Glu Leu Asp Phe
930                 935                 940

Cys Val Leu Arg Pro Cys
945                 950

<210> SEQ ID NO 2
<211> LENGTH: 2853
<212> TYPE: DNA
<213> ORGANISM: Homo sapiens
```

<400> SEQUENCE: 2

```
atgcttttgc tgggcatcct aaccctggct ttcgccgggc gaaccgctgg aggctttgag      60
ccagagcggg aggtagtcgt tcccatccga ctgacccgg acattaacgg ccgccgctac     120
tactggcggg gtcccgagga ctccggggat cagggactca ttttcagat cacagcattt     180
caggaggact tttacctaca cctgacgccg gatgctcagt tcttggctcc cgccttctcc     240
actgagcatc tgggcgtccc cctccagggg ctcaccgggg gctcttcaga cctgcgacgc     300
tgcttctatt ctggggacgt gaacgccgag ccggactcgt tcgctgctgt gagcctgtgc     360
ggggggctcc gcggagcctt tggctaccga ggcgccgagt atgtcattag cccgctgccc     420
aatgctagcg cgccggcggc gcagcgcaac agccagggcg cacaccttct ccagcgccgg     480
ggtgttccgg gcgggccttc cggagacccc acctctcgct gcggggtggc ctcgggctgg     540
aaccccgcca tcctacggg cctggaccct acaagccgc ggcgggcggg cttcggggag      600
agtcgtagcc ggcgcaggtc tgggcgcgcc aagcgtttcg tgtctatccc gcggtacgtg     660
gagacgctgg tggtcgcgga cgagtcaatg gtcaagttcc acggcgcgga cctgaacat     720
tatctgctga cgctgctggc aacggcggcg cgactctacc gccatcccag catcctcaac     780
cccatcaaca tcgttgtggt caaggtgctg cttcttagag atcgtgactc cgggcccaag     840
gtcaccggca atgcggccct gacgctgcgc aacttctgtg cctggcagaa gaagctgaac     900
aaagtgagtg acaagcaccc cgagtactgg gacactgcca tcctcttcac caggcaggac     960
ctgtgtggag ccaccacctg tgacaccctg gcatggctc atgtggggtac catgtgtgac    1020
cccaagagaa gctgctctgt cattgaggac gatgggcttc catcagcctt caccactgcc    1080
cacgagctgg ccacgtgtt caacatgccc catgacaatg tgaaagtctg tgaggaggtg    1140
tttgggaagc tccgagccaa ccacatgatg tccccgaccc tcatccagat cgaccgtgcc    1200
aaccctggt cagcctgcag tgctgccatc atcaccgact tcctgacag cgggcacggt    1260
gactgcctcc tggaccaacc cagcaagccc atctccctgc ccgaggatct gccgggcgcc    1320
agctacaccc tgagccagca gtgcgagctg gcttttggcg tgggctccaa gccctgtcct    1380
tacatgcagt actgcaccaa gctgtggtgc accgggaagg ccaagggaca gatggtgtgc    1440
cagacccgcc acttccctg ggccgatggc accagctgtg cgagggcaa gctctgcctc    1500
aaagggcct gcgtggagag acacaacctc aacaagcaca gggtggatgg ttcctgggcc    1560
aaatgggatc cctatggccc ctgctcgcgc acatgtggtg gggcgtgca gctggccagg    1620
aggcagtgca ccaaccccac ccctgccaac gggggcaagt actgcgaggg agtgagggtg    1680
aaataccgat cctgcaacct ggagccctgc cccagctcag cctccggaaa gagcttccgg    1740
gaggagcagt gtgaggcttt caacggctac aaccacagca ccaaccggct cactctcgcc    1800
gtggcatggg tgcccaagta ctccggcgtg tctccccggg acaagtgcaa gctcatctgc    1860
cgagccaatg gcactggcta cttctatgtg ctggcaccca aggtggtgga cggcacgctg    1920
tgctctcctg actccacctc cgtctgtgtc aaggcaagt gcatcaaggc tggctgtgat    1980
gggaacctgg gctccaagaa gagattcgac aagtgtgggg tgtgtggggg agacaataag    2040
agctgcaaga aggtgactgg actcttcacc aagcccatgc atggctacaa tttcgtggtg    2100
gccatccccg caggcgcctc aagcatcgac atccgccagc gcggttacaa agggctgatc    2160
ggggatgaca actacctggc tctgaagaac agccaaggca gtacctgct caacgggcat    2220
ttcgtggtgt cggcggtgga gcgggacctg gtggtgaagg gcagtctgct gcggtacagc    2280
ggcacgggca cagcggtgga gagcctgcag gcttcccggc ccatcctgga gccgctgacc    2340
```

-continued

```
gtggaggtcc tctccgtggg aagatgaca ccgccccggg tccgctactc cttctatctg    2400
cccaaagagc ctcgggagga caagtcctct catcccaagg accccgggg accctctgtc    2460 ttgcacaaca gcgtcctcag cctctccaac caggtggagc agccggacga caggcccct    2520 gcacgctggg tggctggcag ctgggggccg tgctccgcga gctgcggcag tggcctgcag    2580
aagcgggcgg tggactgccg gggctccgcc gggcagcgca cggtccctgc ctgtgatgca    2640
gcccatcggc ccgtggagac acaagcctgc ggggagccct gccccacctg ggagctcagc    2700
gcctggtcac cctgctccaa gagctgcggc cggggatttc agaggcgctc actcaagtgt    2760
gtgggccacg gaggccggct gctggcccgg gaccagtgca acttgcaccg caagccccag    2820
gagctggact tctgcgtcct gaggccgtgc tga                                2853
```

<210> SEQ ID NO 3
<211> LENGTH: 50
<212> TYPE: DNA
<213> ORGANISM: Homo sapiens

<400> SEQUENCE: 3

```
ctagcgcggc cgcaggatcc gactacaagg acgacgatga caaatgataa                50
```

<210> SEQ ID NO 4
<211> LENGTH: 50
<212> TYPE: DNA
<213> ORGANISM: Homo sapiens

<400> SEQUENCE: 4

```
gatcttatca tttgtcatcg tcgtccttgt agtcggatcc tgcggccgcg                50
```

<210> SEQ ID NO 5
<211> LENGTH: 34
<212> TYPE: DNA
<213> ORGANISM: Homo sapiens

<400> SEQUENCE: 5

```
ggactagtct agaagctggg taccagctgc tagc                                 34
```

<210> SEQ ID NO 6
<211> LENGTH: 29
<212> TYPE: DNA
<213> ORGANISM: Homo sapiens

<400> SEQUENCE: 6

```
ggactagtgt cgaccggtca tggctgcgc                                       29
```

<210> SEQ ID NO 7
<211> LENGTH: 42
<212> TYPE: DNA
<213> ORGANISM: Homo sapiens

<400> SEQUENCE: 7

```
gtgtctagag ccatgctttt gctgggcatc ctaaccctgg ct                        42
```

<210> SEQ ID NO 8
<211> LENGTH: 41
<212> TYPE: DNA
<213> ORGANISM: Homo sapiens

<400> SEQUENCE: 8

```
agagcggccg cctgctcctc ccggaagctc tttccggagg c                         41
```

<210> SEQ ID NO 9
<211> LENGTH: 27
<212> TYPE: DNA
<213> ORGANISM: Homo sapiens

<400> SEQUENCE: 9
aagcacaggg tggatggttc ctgggcc                                27

<210> SEQ ID NO 10
<211> LENGTH: 37
<212> TYPE: DNA
<213> ORGANISM: Homo sapiens

<400> SEQUENCE: 10
gcgcggccgc gcacggcctc aggacgcaga agtccag                     37

<210> SEQ ID NO 11
<211> LENGTH: 37
<212> TYPE: DNA
<213> ORGANISM: Homo sapiens

<400> SEQUENCE: 11
taggatcctt gtagaaactt cagaccatga caactcg                     37

<210> SEQ ID NO 12
<211> LENGTH: 59
<212> TYPE: DNA
<213> ORGANISM: Homo sapiens

<400> SEQUENCE: 12
atggatcctc aatggtgatg gtgatgatga ccgaagcaga aggcatggtg ccgggacag    59

<210> SEQ ID NO 13
<211> LENGTH: 97
<212> TYPE: DNA
<213> ORGANISM: Homo sapiens

<400> SEQUENCE: 13
agcttgccac catgaagacg atcatcgccc tgagctacat cttctgcctg gtattcgccg   60
actacaagga cgatgatgac aagggatcc actagtc                            97

<210> SEQ ID NO 14
<211> LENGTH: 97
<212> TYPE: DNA
<213> ORGANISM: Homo sapiens

<400> SEQUENCE: 14
tcgagactag tggatcccct tgtcatcatc gtccttgtag tcggcgaata ccaggcagaa   60
gatgtagctc agggcgatga tcgtcttcat ggtggca                           97

<210> SEQ ID NO 15
<211> LENGTH: 30
<212> TYPE: DNA
<213> ORGANISM: Homo sapiens

<400> SEQUENCE: 15
acctcagcag ccagctcccct tgtatacaca                            30

<210> SEQ ID NO 16
<211> LENGTH: 30
<212> TYPE: DNA
<213> ORGANISM: Homo sapiens

<400> SEQUENCE: 16
cttgaggggg atggaccaat acagctttgg                                30

<210> SEQ ID NO 17
<211> LENGTH: 38
<212> TYPE: DNA
<213> ORGANISM: Homo sapiens

<400> SEQUENCE: 17
agagcggccg ctccagtcac cttcttgcag ctcttatt                       38

<210> SEQ ID NO 18
<211> LENGTH: 27
<212> TYPE: DNA
<213> ORGANISM: Homo sapiens

<400> SEQUENCE: 18
gcggacgagt ccatggtcaa gttccac                                   27

<210> SEQ ID NO 19
<211> LENGTH: 27
<212> TYPE: DNA
<213> ORGANISM: Homo sapiens

<400> SEQUENCE: 19
ttctgccagg cgcagaagtt gcgcagc                                   27

<210> SEQ ID NO 20
<211> LENGTH: 22
<212> TYPE: DNA
<213> ORGANISM: Homo sapiens

<400> SEQUENCE: 20
gtaatacgac tcactatagg gc                                        22

<210> SEQ ID NO 21
<211> LENGTH: 19
<212> TYPE: DNA
<213> ORGANISM: Homo sapiens

<400> SEQUENCE: 21
actatagggc acgcgtggt                                            19

<210> SEQ ID NO 22
<211> LENGTH: 30
<212> TYPE: DNA
<213> ORGANISM: Homo sapiens

<400> SEQUENCE: 22
actgagcatc cggcgtcagg tgtaggtaaa                                30

<210> SEQ ID NO 23
<211> LENGTH: 30
<212> TYPE: DNA
<213> ORGANISM: Homo sapiens

<400> SEQUENCE: 23
agtcctcctg aaatgctgtg atctgaaaaa                                30

<210> SEQ ID NO 24
<211> LENGTH: 3473
<212> TYPE: DNA

<213> ORGANISM: Homo sapiens
<220> FEATURE:
<221> NAME/KEY: promoter
<222> LOCATION: (1)..(3473)
<223> OTHER INFORMATION:

<400> SEQUENCE: 24

| | | | | | |
|---|---|---|---|---|---|
| ttgcacagct | aagatctggt | ggaggcatgc | acacagggcc | ctctgaccat | gggctctaaa | 60 |
| tcactgtact | atgttccctt | ccataggcct | caatcagtca | tgtaatattt | gacctggtcg | 120 |
| ttatcttagg | tattatctag | accacagatt | ttggatgcag | ttctctggct | gaagacctct | 180 |
| gagctaggat | aaccccttct | cttttgacag | acgagtcaga | gaatcagatc | agtgatagaa | 240 |
| gtggagtgcc | aatcctgagt | atcacctcta | ctcaagtgct | caacatatcc | ctagatcctc | 300 |
| aattccctgg | caaaagtgat | tggatggaac | cacaggcttc | caagagggga | cagtcaagca | 360 |
| ttaaatacga | gaatgcacat | ataactcttg | gtgcaatgtt | tagcacatac | taagcctgca | 420 |
| atacatgcta | atccctttga | gcaaatccac | atggccagtt | tctgtgctca | ggggtgagaa | 480 |
| tagctgggct | gtgattgggg | caggggagc | actaagtggg | agggacttcc | tgtctcaggt | 540 |
| ccctgccatc | ttgactgaca | tgctgcagcc | cttgccaaaa | cccatgggtc | agaatgaaag | 600 |
| taaagtgccg | ttgaaaacct | tgcaatccac | ctttaaaact | gccgggtgta | gtaaaacaat | 660 |
| tgcttgcccc | aaataaatga | cttatcattg | ctgttggttg | tctgcgtttc | tctttaatta | 720 |
| taggccctct | ttgaacgctc | aaacacacag | ggcctttgta | agcttgaact | ccctgtctca | 780 |
| cacacagtcc | tcccataccc | atacactctc | tttcatttgc | agagtataaa | cacccatctc | 840 |
| tcactcattc | acataatgaa | tttcagctcc | ttgtgtccca | atcaaggaga | ggcctcactg | 900 |
| gaattatggg | catctgagcc | atcttcatgt | tccaaggccc | caggggggcgc | ttccaagagt | 960 |
| ggatccttta | tggggagaag | ataatgggca | aaaagtgctc | ttcactgatg | gaccagtccc | 1020 |
| agccttttct | ctccttggac | aatagagttc | ttcccttgaa | cagccacttc | cctaaaaaaa | 1080 |
| attccaaaat | tctcccacat | catcccccttt | atgcttaaaa | tcatcacaca | ctcccttctt | 1140 |
| tgtcctcccc | tcttgcaaac | tcaactcaga | gcccttggc | tccagaaaga | ttttctaggt | 1200 |
| atcaggagag | agtagcaaag | cctccctcct | ctccttgcct | ttctcccttg | tcagagaaag | 1260 |
| aagttgattc | tgcggagagg | taagaaggat | cttgaggtct | agagcctgaa | aaactccttg | 1320 |
| ggctgttctc | caaactagat | gggaacataa | ggtgcgattg | catcttctcc | agctgatact | 1380 |
| cactcggcct | cctatgccag | tccccagtcc | agggtttggt | caagggtcaa | atgagataat | 1440 |
| ttcatggagg | aagcctggcc | cgattttcct | actgtttgct | ggaagacagc | ctcttcctct | 1500 |
| tgtaactgca | gccccagaac | ctgatctcca | catccctgcc | aggcaggtag | ctgtgtacaa | 1560 |
| gggctcatct | tcctgccccc | aacccagct | ctgatttgct | tattcaggtg | gtgtaaatac | 1620 |
| ttctaccagg | acctatttca | agccattgtg | atgtccctga | ctggggagat | gcagggcagc | 1680 |
| acaccattta | atatttccct | cacatttcca | ccccattctg | cactcttttc | tgggagttgc | 1740 |
| tgtctcagag | ggttggcggt | tctggtggct | caagaccata | agtaattatc | aaatacttag | 1800 |
| gaagcgacgg | gttttgagta | tttattacct | tttaaaaatg | tactttgtgg | ctaggcatgg | 1860 |
| tggctcacgc | ctgtagtccc | cgcaccggga | ggccgaggtg | ggtggattgc | ttgagctcag | 1920 |
| gagttcaaga | ccagcctggg | caacacggcg | aaacccagtc | tctaccaaaa | atacacacac | 1980 |
| acacacacac | acacacacac | acacacacac | acacacacac | acacacaaat | tggcctagcg | 2040 |
| tggtgtcgtg | tgtctgtggt | cgcagttact | caggagacca | aggtaggagg | taggaaacca | 2100 |
| aggtaggagg | atcacccgag | gtcggtagtt | cgagaccagc | ctgaccaaca | tggagaaacc | 2160 |

```
ctgtctttac taaaaataca aaattagctg gcgtggtgg tgcatgcctg taattccagc    2220
tacttgggag gctgagacag gagaatggct tgaacccgga aggcggagtt tgcggtgagc    2280
tgagatcgcg tcattgcact ccagcctggg caacaagagc aaaactccgt ctcaaaaaaa    2340 aagaaaatata tatatatatg tgtgtgtgtg tgtgtgtgtg tgtatgtata tatatatatg    2400
tatgtgtata tatatgtatg tgtgtgtgtg tgcatatata tatatacact ttgtttaatt    2460
gtaagtgtgt ttagtttaat ttttaataat gtccgtgatt aacagctggc tggcaagatt    2520
cctgagaact gaagagtttg ccccagccca tccagcacac catgggccca gggcagacct    2580
tggggctagg cggtcttggg ttccagaggg ctcccatgcc cctgtcctat tgctcttctg    2640
gcaataggac atttacgcgg ggggggggg tggttcttga ttctgggtct tttagggggac    2700 tctgtgatta agaaacagca gggatgttgc aacagcaggg atgaggtggg cctggggacg    2760
ggtcagtgaa gggtcttcat tcctagctgc tgacctgatc tgccctgaga taaaagacta    2820
agacccagag agtgaacgct gtccgcgggg gcagaagcga gtgaggcgtc gggacagtgg    2880
ggcataacca agagcaaaac gcaaactgag acttcagcgc cggtttctcg gccagccca    2940 cgcctcctgc ctcagctcaa tgccactccc tccccgccaa gtggctctcc gctctggagg    3000
cgggaccgag ttctccggtg gcccctggag gctccggcag cgagctctgg gaggctggga    3060
ggggagtgag gggagggggcg ctgactgggc cgtccaaaga ggaggggccc tttaataggc    3120
tcgcccagcg cctggcttgc tgcgctgcga gtggctgcgg ttgcgagaag ccgcccggca    3180
ccttccgcta gttctcggct gcaaatcttc gtccttgcac ttgacagcga ttgtacttaa    3240
gctcccaggg cgcgctttgc ttggaaaggc acaggtagga agcgcgggct gccgggtgca    3300
cgctcgccgc cctgggagga gtctccctcc cttggctctc ctttctggga actgccggct    3360
gtcccgtagc gttggcggtt ccagagtgcg ggctgcacgg agaccgcggc agcggccgga    3420
gagcccggcc cagcccttc ccacagcgcg gcggtgcgct gcccggcgcc atg    3473
```

<210> SEQ ID NO 25
<211> LENGTH: 3467
<212> TYPE: DNA
<213> ORGANISM: Homo sapiens
<220> FEATURE:
<221> NAME/KEY: promoter
<222> LOCATION: (1)..(3467)
<223> OTHER INFORMATION:

<400> SEQUENCE: 25

```
ttgcacagct aagatctggt ggaggcatgc acacagggcc ctctgaccat gggctctaaa     60
tcactgtact atgttccctt ccataggcct caatcagtca tgtaatattt gacctggtcg    120
ttatcttagg tattatctag accacagatt ttggatgcag ttctctggct gaagacctct    180
gagctaggat aaccccttct cttttgacag acgagtcaga gaatcagatc agtgatagaa    240
gtggagtgcc aatcctgagt atcacctcta ctcaagtgct caacatatcc ctagatcctc    300
aattccctgg caaaagtgat tggatggaac cacaggcttc aagaggggga cagtcaagca    360
ttaaatacga gaatgcacat ataactcttg gtgcaatgtt tagcacatac taagcctgca    420
atacatgcta atccctttga gcaaatccac atggccagtt tctgtgctca ggggtgagaa    480
tagctgggct gtgattgggg caggggagc actaagtggg agggacttcc tgtctcaggt    540
ccctgccatc ttgactgaca tgctgcagcc cttgccaaaa cccatgggtc agaatgaaag    600
taaagtgccg ttgaaaacct tgcaatccac ctttaaaact gccgggtgta gtaaaacaat    660
```

| | |
|---|---|
| tgcttgcccc aaataaatga cttatcattg ctgttggttg tctgcgtttc tctttaatta | 720 |
| taggccctct ttgaacgctc aaacacacag ggcctttgta agcttgaact ccctgtctca | 780 |
| cacacagtcc tcccataccc atacactctc tttcatttgc agagtataaa cacccatctc | 840 |
| tcactcattc acataatgaa tttcagctcc ttgtgtccca atcaaggaga ggcctcactg | 900 |
| gaattatggg catctgagcc atcttcatgt tccaaggccc caggggggcgc ttccaagagt | 960 |
| ggatccttta tggggagaag ataatgggca aaaagtgctc ttcactgatg gaccagtccc | 1020 |
| agccttttct ctccttggac aatagagttc ttcccttgaa cagccacttc cctaaaaaaa | 1080 |
| attccaaaat tctcccacat catccccttt atgcttaaaa tcatcacaca ctcccttctt | 1140 |
| tgtcctcccc tcttgcaaac tcaactcaga gcccttggc tccagaaaga ttttctaggt | 1200 |
| atcaggagag agtagcaaag cctccctcct ctccttgcct ttctcccttg tcagagaaag | 1260 |
| aagttgattc tgcggagagg taagaaggat cttgaggtct agagcctgaa aaactccttg | 1320 |
| ggctgttctc caaactagat gggaacataa ggtgcgattg catcttctcc agctgatact | 1380 |
| cactcggcct cctatgccag tccccagtcc agggtttggt caagggtcaa atgagataat | 1440 |
| ttcatggagg aagcctggcc cgattttct actgtttgct ggaagacagc ctcttcctct | 1500 |
| tgtaactgca gccccagaac ctgatctcca catccctgcc aggcaggtag ctgtgtacaa | 1560 |
| gggctcatct tcctgccccc aacccagct ctgatttgct tattcaggtg gtgtaaatac | 1620 |
| ttctaccagg acctatttca agccattgtg atgtccctga ctggggagat gcagggcagc | 1680 |
| acaccattta atatttccct cacatttcca ccccattctg cactcttttc tgggagttgc | 1740 |
| tgtctcagag ggttggcggt tctggtggct caagaccata agtaattatc aaatacttag | 1800 |
| gaagcgacgg gttttgagta tttattacct tttaaaaatg tactttgtgg ctaggcatgg | 1860 |
| tggctcacgc ctgtagtccc cgcaccggga ggccgaggtg ggtggattgc ttgagctcag | 1920 |
| gagttcaaga ccagcctggg caacacgcg aaacccagtc tctaccaaaa atacacacac | 1980 |
| acacacacac acacacacac acacacacac acacacacac aaattggcct agcgtggtgt | 2040 |
| cgtgtgtctg tggtcgcagt tactcaggag accaaggtag gaggtaggaa accaaggtag | 2100 |
| gaggatcacc cgaggtcggt agttcgagac cagcctgacc aacatggaga aaccctgtct | 2160 |
| ttactaaaaa tacaaaatta gctgggcgtg gtggtgcatg cctgtaattc cagctacttg | 2220 |
| ggaggctgag acaggagaat ggcttgaacc cggaaggcgg agtttgcggt gagctgagat | 2280 |
| cgcgtcattg cactccagcc tgggcaacaa gagcaaaact ccgtctcaaa aaaaagaaa | 2340 |
| tatatatata tatgtgtgtg tgtgtgtgtg tgtgtatg tatatatata tatgtatgtg | 2400 |
| tatatatatg tatgtgtgtg tgtgtgcata tatatatata cactttgttt aattgtaagt | 2460 |
| gtgtttagtt taattttaa taatgtccgt gattaacagc tggctggcaa gattcctgag | 2520 |
| aactgaagag tttgccccag cccatccagc acaccatggg cccagggcag accttggggc | 2580 |
| taggcggtct tgggttccag agggctccca tgcccctgtc ctattgctct tctggcaata | 2640 |
| ggacatttac gcgggggggg gggtggttc ttgattctgg gtcttttagg ggactctgtg | 2700 |
| attaagaaac agcagggatg ttgcaacagc agggatgagg tgggcctggg gacgggtcag | 2760 |
| tgaagggtct tcattcctag ctgctgacct gatctgccct gagataaaag actaagaccc | 2820 |
| agagagtgaa cgctgtccgc ggggcagaa gcgagtgagg cgtcgggaca gtggggcata | 2880 |
| accaagagca aaacgcaaac tgagacttca gcgccggttt ctcgggccag cccacgcctc | 2940 |
| ctgcctcagc tcaatgccac tccctccccg ccaagtggct ctccgctctg gaggcgggac | 3000 |
| cgagttctcc ggtggcccct ggaggctccg gcagcgagct ctgggaggct gggaggggag | 3060 |

-continued

```
tgaggggagg ggcgctgact gggccgtcca aagaggaggg ggcctttaat aggctcgccc    3120
agcgcctggc ttgctgcgct gcgagtggct gcggttgcga gaagccgccc ggcaccttcc    3180
gctagttctc ggctgcaaat cttcgtcctt gcacttgaca gcgattgtac ttaagctccc    3240
agggcgcgct ttgcttggaa aggcacaggt aggaagcgcg ggctgccggg tgcacgctcg    3300
ccgccctggg aggagtctcc ctcccttggc tctcctttct gggaactgcc ggctgtcccg    3360
tagcgttggc ggttccagag tgcgggctgc acggagaccg cggcagcggc cggagagccc    3420
ggcccagccc cttcccacag cgcggcggtg cgctgcccgg cgccatg                 3467

<210> SEQ ID NO 26
<211> LENGTH: 3464
<212> TYPE: DNA
<213> ORGANISM: Homo sapiens
<220> FEATURE:
<221> NAME/KEY: promoter
<222> LOCATION: (1)..(3464)
<223> OTHER INFORMATION:

<400> SEQUENCE: 26
ttgcacagct aagatctggt ggaggcatgc acacagggcc ctctgaccat ggctctaaa      60 tcactgtact atgttcccTT ccataggcct caatcagtca tgtaatattt gacctggtcg    120
ttatcttagg tattatctag accacagatt ttggatgcag ttctctggct gaagacctct    180
gagctaggat aacccttct cttttgacag acgagtcaga gaatcagatc agtgatagaa     240
gtggagtgcc aatcctgagt atcacctcta ctcaagtgct caacatatcc ctagatcctc    300
aattccctgg caaaagtgat tggatggaac cacaggcttc caagagggga cagtcaagca    360
ttaaatacga gaatgcacat ataactcttg gtgcaatgtt tagcacatac taagcctgca    420
atacatgcta atccctttga gcaaatccac atggccagtt tctgtgctca ggggtgagaa    480
tagctgggct gtgattgggg caggggagc actaagtggg agggacttcc tgtctcaggt     540
ccctgccatc ttgactgaca tgctgcagcc cttgccaaaa cccatgggtc agaatgaaag    600
taaagtgccg ttgaaaacct tgcaatccac ctttaaaact gccgggtgta gtaaaacaat    660
tgcttgcccc aaataaatga cttatcattg ctgttggttg tctgcgtttc tctttaatta    720
taggccctct ttgaacgctc aaacacacag ggcctttgta agcttgaact ccctgtctca    780
cacacagtcc tcccataccc atacactctc tttcatttgc agagtataaa cacccatctc    840
tcactcattc acataatgaa tttcagctcc ttgtgtccca atcaaggaga ggcctcactg    900
gaattatggg catctgagcc atcttcatgt tccaaggccc caggggcgc ttccaagagt     960 ggatccttta tggggagaag ataatgggca aaaagtgctc ttcactgatg gaccagtccc   1020 agcctttct ctccttggac aatagagttc ttcccttgaa cagccacttc cctaaaaaaa    1080
attccaaaat tctcccacat catcccctTT atgcttaaaa tcatcacaca ctcccttctt    1140
tgtcctcccc tcttgcaaac tcaactcaga gcccttTggc tccagaaaga ttttctaggt    1200
atcaggagag agtagcaaag cctccctcct tccttgcct ttctcccttg tcagagaaag    1260
aagttgattc tgcggagagg taagaaggat cttgaggtct agagcctgaa aaactccttg    1320
ggctgttctc caaactagat gggaacataa ggtgcgattg catcttctcc agctgatact    1380
cactcggcct cctatgccag tccccagtcc agggtttggt caagggtcaa atgagataat    1440
ttcatggagg aagcctggcc cgattttttct actgtttgct ggaagacagc ctcttcctct    1500
tgtaactgca gccccagaac ctgatctcca catccctgcc aggcaggtag ctgtgtacaa    1560
```

-continued

```
gggctcatct tcctgccccc aaccccagct ctgatttgct tattcaggtg gtgtaaatac    1620
ttctaccagg acctatttca agccattgtg atgtccctga ctggggagat gcagggcagc    1680
acaccattta atatttccct cacatttcca ccccattctg cactcttttc tgggagttgc    1740
tgtctcagag ggttggcggt tctggtggct caagaccata agtaattatc aaatacttag    1800
gaagcgacgg gttttgagta tttattacct tttaaaaatg tactttgtgg ctaggcatgg    1860
tggctcacgc ctgtagtccc cgcaccggga ggccgaggtg ggtggattgc ttgagctcag    1920
gagttcaaga ccagcctggg caacacggcg aaacccagtc tctaccaaaa atacacacac    1980
acacacacac acacacacac acacacacac acacacacaa attggcctag cgtggtgtcg    2040
tgtgtctgtg gtcgcagtta ctcaggagac caaggtagga ggtaggaaac caaggtagga    2100
ggatcacccg aggtcggtag ttcgagacca gcctgaccaa catggagaaa ccctgtcttt    2160
actaaaaata caaaattagc tgggcgtggt ggtgcatgcc tgtaattcca gctacttggg    2220
aggctgagac aggagaatgg cttgaacccg gaaggcggag tttgcggtga gctgagatcg    2280
cgtcattgca ctccagcctg gcaacaagag caaaactcc gtctcaaaaa aaagaaata    2340 tatatatata tatgtgtgtg tgtgtgtgtg tgtgtatg tatatatata tatgtatgtg     2400
tatatatatg tatgtgtgtg tgtgtgcata tatatataca ctttgtttaa ttgtaagtgt    2460
gtttagttta attttaata atgtccgtga ttaacagctg gctggcaaga ttcctgagaa    2520
ctgaagagtt tgccccagcc catccagcac accatgggcc cagggcagac cttggggcta    2580
ggcggtcttg ggttccagag ggctcccatg cccctgtcct attgctcttc tggcaatagg    2640
acatttacgc gggggggggg gtggttcttg attctgggtc ttttagggga ctctgtgatt    2700
aagaaacagc agggatgttg caacagcagg gatgaggtgg gcctggggac gggtcagtga    2760
agggtcttca ttcctagctg ctgacctgat ctgccctgag ataaaagact aagacccaga    2820
gagtgaacgc tgtccgcggg ggcagaagcg agtgaggcgt cgggacagtg gggcataacc    2880
aagagcaaaa cgcaaactga gacttcagcg ccggtttctc gggccagccc acgcctcctg    2940
cctcagctca atgccactcc ctccccgcca agtggctctc cgctctggag gcgggaccga    3000
gttctccggt ggcccctgga ggctccggca gcgagctctg ggaggctggg aggggagtga    3060
ggggaggggc gctgactggg ccgtccaaag aggagggggc cttaataggc ctcgcccagc    3120
gcctggcttg ctgcgctgcg agtggctgcg gttgcgagaa gccgccggc accttccgct    3180 agttctcggc tgcaaatctt cgtccttgca cttgacagcg attgtactta agctcccagg    3240
gcgcgctttg cttggaaagg cacaggtagg aagcgcgggc tgccgggtgc acgctcgccg    3300
ccctgggagg agtctccctc ccttggctct cctttctggg aactgccggc tgtcccgtag    3360
cgttggcggt tccagagtgc gggctgcacg gagaccgcgg cagcggccgg agagcccggc    3420 ccagccccctt cccacagcgc ggcggtgcgc tgcccggcgc catg                    3464
```

<210> SEQ ID NO 27
<211> LENGTH: 3469
<212> TYPE: DNA
<213> ORGANISM: Homo sapiens
<220> FEATURE:
<221> NAME/KEY: promoter
<222> LOCATION: (1)..(3469)
<223> OTHER INFORMATION:

<400> SEQUENCE: 27

```
ttgcacagct aagatctggt ggaggcatgc acacagggcc ctctgaccat gggctctaaa      60
tcactgtact atgttccctt ccataggcct caatcagtca tgtaatattt gacctggtcg     120
```

-continued

```
ttatcttagg tattatctag accacagatt ttggatgcag ttctctggct gaagacctct    180
gagctaggat aacccttct cttttgacag acgagtcaga gaatcagatc agtgatagaa    240
gtggagtgcc aatcctgagt atcacctcta ctcaagtgct caacatatcc ctagatcctc    300
aattccctgg caaaagtgat tggatggaac cacaggcttc caagaggga cagtcaagca    360
ttaaatacga gaatgcacat ataactcttg gtgcaatgtt tagcacatac taagcctgca    420
atacatgcta atccctttga gcaaatccac atggccagtt tctgtgctca ggggtgagaa    480
tagctgggct gtgattgggg caggggagc actaagtggg agggacttcc tgtctcaggt    540
ccctgccatc ttgactgaca tgctgcagcc cttgccaaaa cccatgggtc agaatgaaag    600
taaagtgccg ttgaaaacct tgcaatccac ctttaaaact gccgggtgta gtaaaacaat    660
tgcttgcccc aaataaatga cttatcattg ctgttggttg tctgcgtttc tctttaatta    720
taggccctct ttgaacgctc aaacacacag ggcctttgta agcttgaact ccctgtctca    780
cacacagtcc tcccataccc atacactctc tttcatttgc agagtataaa cacccatctc    840
tcactcattc acataatgaa tttcagctcc ttgtgtccca atcaaggaga ggcctcactg    900
gaattatggg catctgagcc atcttcatgt tccaaggccc caggggcgc ttccaagagt    960
ggatccttta tggggagaag ataatgggca aaagtgctc ttcactgatg gaccagtccc   1020
agccttttct ctccttggac aatagagttc ttcccttgaa cagccacttc cctaaaaaaa   1080
attccaaaat tctcccacat catccccttt atgcttaaaa tcatcacaca ctcccttctt   1140
tgtcctcccc tcttgcaaac tcaactcaga gcccttggc tccagaaaga ttttctaggt   1200
atcaggagag agtagcaaag cctccctcct ctccttgcct ttctcccttg tcagagaaag   1260
aagttgattc tgcggagagg taagaaggat cttgaggtct agagcctgaa aaactccttg   1320
ggctgttctc caaactagat gggaacataa ggtgcgattg catcttctcc agctgatact   1380
cactcggcct cctatgccag tccccagtcc agggtttggt caagggtcaa atgagataat   1440
ttcatggagg aagcctggcc cgattttct actgtttgct ggaagacagc ctcttcctct   1500
tgtaactgca gccccagaac ctgatctcca catccctgcc aggcaggtag ctgtgtacaa   1560
gggctcatct tcctgccccc aaccccagct ctgatttgct tattcaggtg gtgtaaatac   1620
ttctaccagg acctatttca agccattgtg atgtccctga ctggggagat gcagggcagc   1680
acaccattta atatttccct cacatttcca ccccattctg cactctttc tgggagttgc   1740
tgtctcagag ggttggcggt tctggtggct caagaccata agtaattatc aaatacttag   1800
gaagcgacgg gttttgagta tttattacct tttaaaaatg tactttgtgg ctaggcatgg   1860
tggctcacgc ctgtagtccc cgcaccggga ggccgaggtg ggtggattgc ttgagctcag   1920
gagttcaaga ccagcctggg caacacggcg aaacccagtc tctaccaaaa atacacacac   1980
acacacacac acacacacac acacacacac acacacacac acaaattggc ctagcgtggt   2040
gtcgtgtgtc tgtggtcgca gttactcagg agaccaaggt aggaggtagg aaaccaaggt   2100
aggaggatca cccgaggtcg gtagttcgag accagcctga ccaacatgga gaaaccctgt   2160
ctttactaaa aatacaaaat tagctgggcg tggtggtgca tgcctgtaat tccagctact   2220
tgggaggctg agacaggaga atggcttgaa cccggaaggc ggagtttgcg gtgagctgag   2280
atcgcgtcat tgcactccag cctgggcaac aagagcaaaa ctccgtctca aaaaaaaaga   2340
aatatatata tatgtgtgtg tgtgtgtgtg tgtgtgtgta tgtatatata tatatgtatg   2400
tgtatatata tgtatgtgtg tgtgtgtgca tatatatata tacactttgt ttaattgtaa   2460
```

-continued

```
gtgtgtttag tttaattttt aataatgtcc gtgattaaca gctggctggc aagattcctg    2520
agaactgaag agtttgcccc agcccatcca gcacaccatg ggcccagggc agaccttggg    2580
gctaggcggt cttgggttcc agagggctcc catgcccctg tcctattgct cttctggcaa    2640
taggacattt acgcggggg gggggtggt tcttgattct gggtctttta ggggactctg     2700
tgattaagaa acagcaggga tgttgcaaca gcagggatga ggtgggcctg ggacgggtc     2760 agtgaagggt cttcattcct agctgctgac ctgatctgcc ctgagataaa agactaagac    2820
ccagagagtg aacgctgtcc gcgggggcag aagcgagtga ggcgtcggga cagtggggca    2880
taaccaagag caaaacgcaa actgagactt cagcgccggt ttctcgggcc agcccacgcc    2940
tcctgcctca gctcaatgcc actccctccc cgccaagtgg ctctccgctc tggaggcggg    3000
accgagttct ccggtggccc ctggaggctc cggcagcgag ctctgggagg ctgggagggg    3060
agtgagggga ggggcgctga ctgggccgtc caaagaggag ggggccttta ataggctcgc    3120
ccagcgcctg gcttgctgcg ctgcgagtgg ctgcggttgc gagaagccgc ccggcacctt    3180
ccgctagttc tcggctgcaa atcttcgtcc ttgcacttga cagcgattgt acttaagctc    3240
ccagggcgcg ctttgcttgg aaaggcacag gtaggaagcg cgggctgccg ggtgcacgct    3300
cgccgccctg ggaggagtct ccctcccttg gctctccttt ctgggaactg ccggctgtcc    3360
cgtagcgttg gcggttccag agtgcgggct gcacggagac cgcggcagcg gccggagagc    3420
ccggcccagc cccttcccac agcgcggcgg tgcgctgccc ggcgccatg              3469
```

<210> SEQ ID NO 28
<211> LENGTH: 3470
<212> TYPE: DNA
<213> ORGANISM: Homo sapiens
<220> FEATURE:
<221> NAME/KEY: promoter
<222> LOCATION: (1)..(3470)
<223> OTHER INFORMATION:

<400> SEQUENCE: 28

```
ttgcacagct aagatctggt ggaggcatgc acacagggcc ctctgaccat gggctctaaa      60
tcactgtact atgttccctt ccataggcct caatcagtca tgtaatattt gacctggtcg     120
ttatcttagg tattatctag accacagatt ttggatgcag ttctctggct gaagacctct     180
gagctaggat accccttctc ttttgacaga cgagtcagag aatcagatca gtgatagaag     240
tggagtgcca atcctgagta tcacctctac tcaagtgctc aacatatccc tagatcctca     300
attccctggc aaaagtgatt ggatggaacc acaggcttcc aagaggggac agtcaagcat     360
taaatacgag aatgcacata taactcttgg tgcaatgttt agcacatact aagcctgcaa     420
tacatgctaa tccctttgag caaatccaca tggccagttt ctgtgctcag gggtgagaat     480
agctgggctg tgattgggc aggggagca ctaagtggga gggacttcct gtctcaggtc      540
cctgccatct tgactgacat gctgcagccc ttgccaaaac ccatgggtca gaatgaaagt     600
aaagtgccgt tgaaaccctt gcaatccacc tttaaaactg ccgggtgtag taaaacaatt     660
gcttgcccca ataaatgac ttatcattgc tgttggttgt ctgcgtttct ctttaattat      720
aggccctctt tgaacgctca aacacacagg gcctttgtaa gcttgaactc cctgtctcac     780
acacagtcct cccatacca tacactctct ttcatttgca gagtataaac acccatctct      840
cactcattca cataatgaat ttcagctcct tgtgtcccaa tcaaggagag gcctcactgg     900
aattatgggc atctgagcca tcttcatgtt ccaaggcccc agggggcgct tccaagagtg     960
gatcctttat ggggagaaga taatgggcaa aaagtgctct tcactgatgg accagtccca    1020
```

-continued

```
gcctttctc tccttggaca atagagttct tcccttgaac agccacttcc ctaaaaaaaa    1080
ttccaaaatt ctcccacatc atcccctta tgcttaaaat catcacacac tcccttcttt    1140
gtcctcccct cttgcaaact caactcagag ccctttggct ccagaaagat tttctaggta    1200
tcaggagaga gtagcaaagc ctccctcctc tccttgcctt tctcccttgt cagagaaaga    1260
agttgattct gcggagaggt aagaaggatc ttgaggtcta gagcctgaaa aactccttgg    1320
gctgttctcc aaactagatg ggaacataag gtgcgattgc atcttctcca gctgatactc    1380
actcggcctc ctatgccagt ccccagtcca gggtttggtc aagggtcaaa tgagataatt    1440
tcatggagga agcctggccc gattttttcta ctgtttgctg aagacagcc tcttcctctt    1500 gtaactgcag ccccagaacc tgatctccac atccctgcca ggcaggtagc tgtgtacaag    1560
ggctcatctt cctgccccca accccagctc tgatttgctt attcaggtgg tgtaaatact    1620
tctaccagga cctatttcaa gccattgtga tgtccctgac tggggagatg cagggcagca    1680
caccatttaa tatttccctc acatttccac cccattctgc actcttttct gggagttgct    1740
gtctcagagg gttggcggtt ctggtggctc aagaccataa gtaattatca atacttaggg    1800
aagcgacggg ttttgagtat ttattacctt ttaaaaatgt actttgtggc taggcatggt    1860
ggctcacgcc tgtagtcccc gcaccgggag gccgaggtgg gtggattgct tgagctcagg    1920
agttcaagac cagcctgggc aacacggcga aacccagtct ctaccaaaaa tacacacaca    1980
cacacacaca cacacacaca cacacacaca cacacacaca caaattggcc tagcgtggtg    2040
tcgtgtgtct gtggtcgcag ttactcagga gaccaaggta ggaggtagga aaccaaggta    2100
ggaggatcac ccgaggtcgg tagttcgaga ccagcctgac caacatggag aaaccctgtc    2160
tttactaaaa atacaaaatt agctgggcgt ggtggtgcat gcctgtaatt ccagctactt    2220
gggaggctga dacaggagaa tggcttgaac ccggaaggcg gagtttgcgg tgagctgaga    2280
tcgcgtcatt gcactccagc ctgggcaaca agagcaaaac tccgtctcaa aaaaaaagaa    2340
atatatatat atatgtgtgt gtgtgtgtgt gtgtgtgtat gtatatatat atatgtatgt    2400
gtatatatat gtatgtgtgt gtgtgtgcat atatatatat acactttgtt taattgtaag    2460
tgtgtttagt ttaattttta ataatgtccg tgattaacag ctggctggca agattcctga    2520
gaactgaaga gtttgcccca gcccatccag cacaccatgg gcccagggca gaccttgggg    2580
ctaggcggtc ttgggttcca gagggctccc atgcccctgt cctattgctc ttctggcaat    2640
aggacattta cgcggggggg ggggggggtgg ttcttgattc tgggtctttt agggactct    2700 gtgattaaga aacagcaggg atgttgcaac agcagggatg aggtgggcct ggggacgggt    2760
cagtgaaggg tcttcattcc tagctgctga cctgatctgc cctgagataa aagactaaga    2820
cccagagagt gaacgctgtc cgcggggca gaagcgagtg aggcgtcggg acagtggggc    2880
ataaccaaga gcaaaacgca aactgagact tcagcgccgg tttctcgggc cagcccacgc    2940
ctcctgcctc agctcaatgc cactccctcc ccgccaagtg gctctccgct ctggaggcgg    3000
gaccgagttc tccggtggcc cctggaggct ccggcagcga gctctgggag ctgggaggg    3060 gagtgagggg aggggcgctg actgggccgt ccaaagagga ggggcctttt aataggctcg    3120
cccagcgcct ggcttgctgc gctgcgagtg gctgcgttg cgagaagccg cccggcacct    3180
tccgctagtt ctcggctgca aatcttcgtc cttgcacttg acagcgattg tacttaagct    3240
cccagggcgc gctttgcttg gaaaggcaca ggtaggaagc gcgggctgcc gggtgcacgc    3300
tcgccgccct gggaggagtc tccctcccctt ggctctcctt tctgggaact gccggctgtc    3360
```

-continued

| | |
|---|---|
| ccgtagcgtt ggcggttcca gagtgcgggc tgcacggaga ccgcggcagc ggccggagag | 3420 |
| cccggcccag cccccttccca cagcgcggcg gtgcgctgcc cggcgccatg | 3470 |

<210> SEQ ID NO 29
<211> LENGTH: 3467
<212> TYPE: DNA
<213> ORGANISM: Homo sapiens
<220> FEATURE:
<221> NAME/KEY: promoter
<222> LOCATION: (1)..(3467)
<223> OTHER INFORMATION:

<400> SEQUENCE: 29

| | |
|---|---|
| ttgcacagct aagatctggt ggaggcatgc acacagggcc ctctgaccat gggctctaaa | 60 |
| tcactgtact atgttccctt ccataggcct caatcagtca tgtaatattt gacctggtcg | 120 |
| ttatcttagg tattatctag accacagatt ttggatgcag ttctctggct gaagacctct | 180 |
| gagctaggat aacccccttct cttttgacag acgagtcaga gaatcagatc agtgatagaa | 240 |
| gtggagtgcc aatcctgagt atcacctcta ctcaagtgct caacatatcc ctagatcctc | 300 |
| aattccctgg caaaagtgat tggatggaac cacaggcttc caagagggga cagtcaagca | 360 |
| ttaaatacga gaatgcacat ataactcttg gtgcaatgtt tagcacatac taagcctgca | 420 |
| atacatgcta atccctttga gcaaatccac atggccagtt tctgtgctca ggggtgagaa | 480 |
| tagctgggct gtgattgggg caggggagc actaagtggg agggacttcc tgtctcaggt | 540 |
| ccctgccatc ttgactgaca tgctgcagcc cttgccaaaa cccatgggtc agaatgaaag | 600 |
| taaagtgccg ttgaaaacct tgcaatccac cttaaaact gccgggtgta gtaaaacaat | 660 |
| tgcttgcccc aaataaatga cttatcattg ctgttggttg tctgcgtttc tctttaatta | 720 |
| taggccctct ttgaacgctc aaacacacag ggcctttgta agcttgaact ccctgtctca | 780 |
| cacacagtcc tcccataccc atacactctc tttcatttgc agagtataaa cacccatctc | 840 |
| tcactcattc acataatgaa tttcagctcc ttgtgtccca atcaaggaga ggcctcactg | 900 |
| gaattatggg catctgagcc atcttcatgt tccaaggccc caggggggcgc ttccaagagt | 960 |
| ggatccttta tggggagaag ataatgggca aaaagtgctc ttcactgatg gaccagtccc | 1020 |
| agccttttct ctccttggac aatagagttc ttcccttgaa cagccacttc cctaaaaaaa | 1080 |
| attccaaaat tctcccacat catccccttt atgcttaaaa tcatcacaca ctcccttctt | 1140 |
| tgtcctcccc tcttgcaaac tcaactcaga gcccttttggc tccagaaaga ttttctaggt | 1200 |
| atcaggagag agtagcaaag cctccctcct ctccttgcct ttctcccttg tcagagaaag | 1260 |
| aagttgattc tgcggagagg taagaaggat cttgaggtct agagcctgaa aaactccttg | 1320 |
| ggctgttctc caaactagat gggaacataa ggtgcgattg catcttctcc agctgatact | 1380 |
| cactcggcct cctatgccag tccccagtcc agggtttggt caagggtcaa atgagataat | 1440 |
| ttcatggagg aagcctggcc cgatttttct actgtttgct ggaagacagc ctcttcctct | 1500 |
| tgtaactgca gccccagaac ctgatctcca catccctgcc aggcaggtag ctgtgtacaa | 1560 |
| gggctcatct tcctgccccc aaccccagct ctgatttgct tattcaggtg gtgtaaatac | 1620 |
| ttctaccagg acctatttca agccattgtg atgtccctga ctggggagat gcagggcagc | 1680 |
| acaccattta atatttccct cacatttcca ccccattctg cactctttc tgggagttgc | 1740 |
| tgtctcagag ggttggcggt tctggtggct caagaccata agtaattatc aaatacttag | 1800 |
| gaagcgacgg gttttgagta tttattacct tttaaaaatg tactttgtgg ctaggcatgg | 1860 |
| tggctcacgc ctgtagtccc cgcaccggga ggccgaggtg ggtggattgc ttgagctcag | 1920 |

-continued

```
gagttcaaga ccagcctggg caacacggcg aaacccagtc tctaccaaaa atacacacac    1980
acacacacac acacacacac acacacacac acacacacac acaaattggc ctagcgtggt    2040
gtcgtgtgtc tgtggtcgca gttactcagg agaccaaggt aggaggtagg aaaccaaggt    2100
aggaggatca cccgaggtcg gtagttcgag accagcctga ccaacatgga gaaaccctgt    2160
ctttactaaa aatacaaaat tagctgggcg tggtggtgca tgcctgtaat tccagctact    2220
tgggaggctg agacaggaga atggcttgaa cccggaaggc ggagtttgcg gtgagctgag    2280
atcgcgtcat tgcactccag cctgggcaac aagagcaaaa ctccgtctca aaaaaaaga    2340 aatatatata tatatgtgtg tgtgtgtgtg tgtgtgtgtg tatgtatata tatatatgta    2400
tgtgtatata tatgtatgtg tgtgtgtgtg catatatata tacactttgt ttaattgtaa    2460
gtgtgtttag tttaatttt aataatgtcc gtgattaaca gctggctggc aagattcctg    2520
agaactgaag agtttgcccc agcccatcca gcacaccatg ggcccaggc agaccttggg    2580 gctaggcggt cttgggttcc agagggctcc catgcccctg tcctattgct cttctggcaa    2640
taggacattt acgcgggggg gggtggttc ttgattctgg gtcttttagg ggactctgtg    2700
attaagaaac agcagggatg ttgcaacagc agggatgagg tgggcctggg gacgggtcag    2760
tgaagggtct tcattcctag ctgctgacct gatctgccct gagataaaag actaagaccc    2820
agagagtgaa cgctgtccgc gggggcagaa gcgagtgagg cgtcgggaca gtgggcata    2880 accaagagca aaacgcaaac tgagacttca gcgccggttt ctcgggccag cccacgcctc    2940
ctgcctcagc tcaatgccac tccctccccg ccaagtggcc ctccgctctg gaggcgggac    3000
cgagttctcc ggtggcccct ggaggctccg gcagcgagct ctgggaggct gggagggag    3060 tgagggagg ggcgctgact gggccgtcca agaggagg ggcctttaat aggctcgccc    3120
agcgcctggc ttgctgcgct gcgagtggct gcggttgcga gaagccgccc ggcaccttcc    3180
gctagttctc ggctgcaaat cttcgtcctt gcacttgaca gcgattgtac ttaagctccc    3240
agggcgcgct ttgcttggaa aggcacaggt aggaagcgcg ggctgccggg tgcacgctcg    3300 ccgcctggg aggagtctcc ctcccttggc tctcctttct gggaactgcc ggctgtcccg    3360
tagcgttggc ggttccagag tgcgggctgc acggagaccg cggcagcggc cggagagccc    3420
ggcccagccc cttcccacag cgcggcggtg cgctgcccgg cgccatg    3467
```

<210> SEQ ID NO 30
<211> LENGTH: 3462
<212> TYPE: DNA
<213> ORGANISM: Homo sapiens
<220> FEATURE:
<221> NAME/KEY: promoter
<222> LOCATION: (1)..(3462)
<223> OTHER INFORMATION:

<400> SEQUENCE: 30

```
ttgcacagct aagatctggt ggaggcatgc acacagggcc ctctgaccat gggctctaaa      60
tcactgtact atgttcccctt ccataggcct caatcagtca tgtaatattt gacctggtcg     120
ttatcttagg tattatctag accacagatt ttggatgcag ttctctggct gaagacctct     180
gagctaggat aacccttct cttttgacag acgagtcaga gaatcagatc agtgatagaa       240
gtggagtgcc aatcctgagt atcacctcta ctcaagtgct caacatatcc ctagatcctc     300
aattccctgg caaagtgat tggatggaac cacaggcttc caagagggga cagtcaagca     360
ttaaatacga gaatgcacat ataactcttg gtgcaatgtt tagcacatac taagcctgca    420
```

-continued

| | | |
|---|---|---|
| atacatgcta atccctttga gcaaatccac atggccagtt tctgtgctca ggggtgagaa | 480 |
| tagctgggct gtgattgggg caggggagc actaagtggg agggacttcc tgtctcaggt | 540 |
| ccctgccatc ttgactgaca tgctgcagcc cttgccaaaa cccatgggtc agaatgaaag | 600 |
| taaagtgccg ttgaaaacct tgcaatccac ctttaaaact gccgggtgta gtaaaacaat | 660 |
| tgcttgcccc aaataaatga cttatcattg ctgttggttg tctgcgtttc tctttaatta | 720 |
| taggccctct ttgaacgctc aaacacacag ggcctttgta agcttgaact ccctgtctca | 780 |
| cacacagtcc tcccataccc atacactctc tttcatttgc agagtataaa cacccatctc | 840 |
| tcactcattc acataatgaa tttcagctcc ttgtgtccca atcaaggaga ggcctcactg | 900 |
| gaattatggg catctgagcc atcttcatgt tccaaggccc caggggcgc ttccaagagt | 960 |
| ggatccttta tggggagaag ataatgggca aaaagtgctc ttcactgatg gaccagtccc | 1020 |
| agccttttct ctccttggac aatagagttc ttcccttgaa cagccacttc cctaaaaaaa | 1080 |
| attccaaaat tctcccacat catcccttt atgcttaaaa tcatcacaca ctcccttctt | 1140 |
| tgtcctcccc tcttgcaaac tcaactcaga gccctttggc tccagaaaga ttttctaggt | 1200 |
| atcaggagag agtagcaaag cctccctcct ctccttgcct ttctcccttg tcagagaaag | 1260 |
| aagttgattc tgcggagagg taagaaggat cttgaggtct agagcctgaa aaactccttg | 1320 |
| ggctgttctc caaactagat gggaacataa ggtgcgattg catcttctcc agctgatact | 1380 |
| cactcggcct cctatgccag tccccagtcc agggtttggt caagggtcaa atgagataat | 1440 |
| ttcatggagg aagcctggcc cgattttttct actgtttgct ggaagacagc ctcttcctct | 1500 |
| tgtaactgca gccccagaac ctgatctcca catccctgcc aggcaggtag ctgtgtacaa | 1560 |
| gggctcatct tcctgccccc aaccccagct ctgatttgct tattcaggtg gtgtaaatac | 1620 |
| ttctaccagg acctatttca agccattgtg atgtccctga ctggggagat gcagggcagc | 1680 |
| acaccattta atatttccct cacatttcca ccccattctg cactcttttc tgggagttgc | 1740 |
| tgtctcagag ggttggcggt tctggtggct caagaccata agtaattatc aaatacttag | 1800 |
| gaagcgacgg gttttgagta tttattacct tttaaaaatg tactttgtgg ctaggcatgg | 1860 |
| tggctcacgc ctgtagtccc cgcaccggga ggccgaggtg ggtggattgc ttgagctcag | 1920 |
| gagttcaaga ccagcctggg caacacgcg aaacccagtc tctaccaaaa atacacacac | 1980 |
| acacacacac acacacacac acacacacac acacacacaa attggcctag cgtggtgtcg | 2040 |
| tgtgtctgtg gtcgcagtta ctcaggagac caaggtagga ggtaggaaac caaggtagga | 2100 |
| ggatcacccg aggtcggtag ttcgagacca gcctgaccaa catggagaaa ccctgtcttt | 2160 |
| actaaaaata caaaattagc tgggcgtggt ggtgcatgcc tgtaattcca gctacttggg | 2220 |
| aggctgagac aggagaatgg cttgaacccg gaaggcggag tttgcggtga gctgagatcg | 2280 |
| cgtcattgca ctccagcctg gcaacaaga gcaaaactcc gtctcaaaaa aaagaaata | 2340 |
| tatatatata tgtgtgtgtg tgtgtgtgtg tgtgtatgta tatatatata tgtatgtgta | 2400 |
| tatatatgta tgtgtgtgtg tgtgcatata tatatataca ctttgtttaa ttgtaagtgt | 2460 |
| gtttagttta attttttaata atgtccgtga ttaacagctg gctggcaaga ttcctgagaa | 2520 |
| ctgaagagtt tgccccagcc catccagcac accatgggcc cagggcagac cttgggcta | 2580 |
| ggcggtcttg ggttccagag ggctcccatg cccctgtcct attgctcttc tggcaatagg | 2640 |
| acatttacgc gggggggggt ggttcttgat tctgggtctt ttaggggact ctgtgattaa | 2700 |
| gaaacagcag ggatgttgca acagcaggga tgaggtgggc ctggggacgg gtcagtgaag | 2760 |
| ggtcttcatt cctagctgct gacctgatct gccctgagat aaaagactaa gacccagaga | 2820 |

```
gtgaacgctg tccgcggggg cagaagcgag tgaggcgtcg ggacagtggg gcataaccaa    2880
gagcaaaacg caaactgaga cttcagcgcc ggtttctcgg gccagcccac gcctcctgcc    2940
tcagctcaat gccactccct ccccgccaag tggctctccg ctctggaggc gggaccgagt    3000
tctccggtgg cccctggagg ctccggcagc gagctctggg aggctgggag gggagtgagg    3060
ggaggggcgc tgactgggcc gtccaaagag gagggggcct taataggct cgcccagcgc     3120 ctggcttgct gcgctgcgag tggctgcggt tgcgagaagc cgcccggcac cttccgctag    3180
ttctcggctg caaatcttcg tccttgcact tgacagcgat tgtacttaag ctcccagggc    3240
gcgctttgct tggaaaggca caggtaggaa gcgcgggctg ccgggtgcac gctcgccgcc    3300
ctgggaggag tctccctccc ttggctctcc tttctgggaa ctgccggctg tcccgtagcg    3360
ttggcggttc cagagtgcgg gctgcacgga gaccgcggca gcggccggag agcccggccc    3420
agccccttcc cacagcgcgg cggtgcgctg cccggcgcca tg                       3462

<210> SEQ ID NO 31
<211> LENGTH: 3455
<212> TYPE: DNA
<213> ORGANISM: Homo sapiens
<220> FEATURE:
<221> NAME/KEY: promoter
<222> LOCATION: (1)..(3455)
<223> OTHER INFORMATION:

<400> SEQUENCE: 31
ttgcacagct aagatctggt ggaggcatgc acacagggcc ctctgaccat gggctctaaa      60
tcactgtact atgttccctt ccataggcct caatcagtca tgtaatattt gacctggtcg     120
ttatcttagg tattatctag accacagatt ttggatgcag ttctctggct gaagacctct     180
gagctaggat aaccccttct cttttgacag acgagtcaga gaatcagatc agtgatagaa     240
gtggagtgcc aatcctgagt atcacctcta ctcaagtgct caacatatcc ctagatcctc     300
aattccctgg caaaagtgat tggatggaac cacaggcttc caagagggga cagtcaagca    360
ttaaatacga gaatgcacat ataactcttg gtgcaatgtt tagcacatac taagcctgca    420
atacatgcta atccctttga gcaaatccac atggccagtt tctgtgctca ggggtgagaa    480
tagctgggct gtgattgggg caggggagc actaagtggg agggacttcc tgtctcaggt      540
ccctgccatc ttgactgaca tgctgcagcc cttgccaaaa cccatgggtc agaatgaaag    600
taaagtgccg ttgaaaacct tgcaatccac ctttaaaact gccgggtgta gtaaaacaat    660
tgcttgcccc aaataaatga cttatcattg ctgttggttg tctgcgtttc tctttaatta    720
taggccctct ttgaacgctc aaacacacag ggcctttgta agcttgaact ccctgtctca    780
cacacagtcc tcccataccc atacactctc tttcatttgc agagtataaa cacccatctc    840
tcactcattc acataatgaa tttcagctcc ttgtgtccca atcaaggaga ggcctcactg    900
gaattatggg catctgagcc atcttcatgt tccaaggccc caggggggcgc ttccaagagt    960 ggatccttta tggggagaag ataatgggca aaaagtgctc ttcactgatg gaccagtccc    1020
agccttttct ctccttggac aatagagttc ttcccttgaa cagccacttc cctaaaaaaa    1080
attccaaaat tctcccacat catccccttt atgcttaaaa tcatcacaca ctcccttctt    1140
tgtcctcccc tcttgcaaac tcaactcaga gccctttggc tccagaaaga ttttctaggt    1200
atcaggagag agtagcaaag cctccctcct ctccttgcct ttctcccttg tcagagaaag    1260
aagttgattc tgcggagagg taagaaggat cttgaggtct agagcctgaa aaactccttg    1320
```

```
ggctgttctc caaactagat gggaacataa ggtgcgattg catcttctcc agctgatact    1380
cactcggcct cctatgccag tccccagtcc agggtttggt caagggtcaa atgagataat    1440
ttcatggagg aagcctggcc cgattttcct actgtttgct ggaagacagc ctcttcctct    1500
tgtaactgca gccccagaac ctgatctcca catccctgcc aggcaggtag ctgtgtacaa    1560
gggctcatct tcctgccccc aaccccagct ctgatttgct tattcaggtg gtgtaaatac    1620
ttctaccagg acctatttca agccattgtg atgtccctga ctggggagat gcagggcagc    1680
acaccattta atatttccct cacatttcca ccccattctg cactcttttc tgggagttgc    1740
tgtctcagag ggttggcggt tctggtggct caagaccata agtaattatc aaatacttag    1800
gaagcgacgg gttttgagta tttattacct tttaaaaatg tactttgtgg ctaggcatgg    1860
tggctcacgc ctgtagtccc cgcaccggga ggccgaggtg ggtggattgc ttgagctcag    1920
gagttcaaga ccagcctggg caacacggcg aaacccagtc tctaccaaaa atacacacac    1980
acacacacac acacacacac acacacacac acacacacac acacaaaat tggcctagcg tggtgtcgtg    2040
tgtctgtggt cgcagttact caggagacca aggtaggagg taggaaacca aggtaggagg    2100
atcacccgag gtcggtagtt cgagaccagc ctgaccaaca tggagaaacc ctgtctttac    2160
taaaaataca aaattagctg ggcgtggtgg tgcatgcctg taattccagc tacttgggag    2220
gctgagacag gagaatggct tgaacccgga aggcggagtt tgcggtgagc tgagatcgcg    2280
tcattgcact ccagcctggg caacaagagc aaaactccgt ctcaaaaaaa aaaaaatata    2340
tatatatgtg tgtgtgtgtg tgtgtgtgtg tatgtatata tatatgtata tgtgtatata    2400
tatgtatgtg tgtgtgtgca tatatatata tacactttgt ttaattgtaa gtgtgtttag    2460
tttaattttt aataatgtcc gtgattaaca gctggctggc aagattcctg agaactgaag    2520
agtttgcccc agcccatcca gcacaccatg ggcccagggc agaccttggg gctaggcggt    2580
cttgggttcc agagggctcc catgcccctg tcctattgct cttctggcaa taggacattt    2640
acgcgggggg ggtggttctt gattctgggt cttttagggg actctgtgat taagaaacag    2700
cagggatgtt gcaacagcag ggatgaggtg ggcctgggga cgggtcagtg aagggtcttc    2760
attcctagct gctgacctga tctgccctga gataaaagac taagacccag agagtgaacg    2820
ctgtccgcgg gggcagaagc gagtgaggcg tcgggacagt ggggcataac caagagcaaa    2880
acgcaaactg agacttcagc gccggtttct cgggccagcc cacgcctcct gcctcagctc    2940
aatgccactc cctccccgcc aagtggctct ccgctctgga ggcgggaccg agttctccgg    3000
tggcccctgg aggctccggc agcgagctct gggaggctgg gaggggagtg aggggagggg    3060
cgctgactgg gccgtccaaa gaggaggggg cctttaatag gctcgcccag cgcctggctt    3120
gctgcgctgc gagtggctgc ggttgcgaga agccgcccgg caccttccgc tagttctcgg    3180
ctgcaaatct tcgtccttgc acttgacagc gattgtactt aagctcccag ggcgcgcttt    3240
gcttggaaag gcacaggtag aagcgcggg ctgccgggtg cacgctcgcc gccctgggag    3300
gagtctccct cccttggctc tcctttctgg gaactgccgg ctgtcccgta gcgttggcgg    3360
ttccagagtg cgggctgcac ggagaccgcg gcagcggccg gagagcccgg cccagcccct    3420
tcccacagcg cggcggtgcg ctgcccggcg ccatg                                3455
```

<210> SEQ ID NO 32
<211> LENGTH: 11
<212> TYPE: PRT
<213> ORGANISM: Homo sapiens

<400> SEQUENCE: 32

```
Ala Arg Gly Ser Val Val Leu Thr Ala Lys Cys
1               5                   10

<210> SEQ ID NO 33
<211> LENGTH: 13
<212> TYPE: PRT
<213> ORGANISM: Homo sapiens

<400> SEQUENCE: 33

Gly Ser Ala Ala Ala Asp Tyr Lys Asp Asp Asp Lys
1               5                   10

<210> SEQ ID NO 34
<211> LENGTH: 38
<212> TYPE: DNA
<213> ORGANISM: Homo sapiens

<400> SEQUENCE: 34
agagcggccg cctgctggct cagggtgtag ctggcgcc                              38

<210> SEQ ID NO 35
<211> LENGTH: 38
<212> TYPE: DNA
<213> ORGANISM: Homo sapiens

<400> SEQUENCE: 35
agagcggccg cggaaccatc caccctgtgc ttgttgag                              38
```

METALLOPROTEASE HAVING AGGRECANASE ACTIVITY

TECHNICAL FIELD

This invention relates to a novel metalloprotease having an aggrecanase activity and causing joint diseases (to be referred to as "joint disease aggrecanase" hereinafter), a gene coding for this "joint disease aggrecanase", a method for producing the "joint disease aggrecanase", a method for screening a substance capable of inhibiting the aggrecanase activity with the use of the "joint disease aggrecanase", a pharmaceutical composition for inhibiting degradation of proteoglycans, which comprises the substance capable of inhibiting the aggrecanase activity as the active ingredient, and a promoter gene of the "joint disease aggrecanase".

BACKGROUND ART

Joint diseases are diseases which show damage and degeneration of joint cartilage as the main morbid states. Though a disease having the most frequent number of patients among joint diseases is osteoarthritis (OA), analgesic anti-inflammatory drugs and hyaluronic acid preparations are used in the current therapeutic method merely as a symptomatic therapy for the purpose of alleviating pains accompanied by the degeneration of cartilage and the destruction of bone under cartilage, so that it cannot be said that they are exerting sufficient therapeutic effects.

Joint cartilage is a tissue mainly composed of type II collagen and aggrecan which is a cartilage-specific proteoglycan, and degradation and degeneration of both of them are observed in the joint diseases. Because of this, it has been considered for a long time that control of the degradation and degeneration of these extracellular matrix components would lead to the treatment of joint diseases, so that attempts have been positively made to identify degradation-concerned proteases (collagenase and aggrecanase) and to screen their inhibitors and develop them as medicaments.

As proteases having collagenase activities, matrix metalloproteases (MMP1, MMP8, MMP13, MMP14 and the like) have been identified, and their selective inhibitors have been discovered. However, in spite of the attempts to develop a large number of MMP inhibitors having collagenase inhibition activities as therapeutic drugs for joint diseases including OA and rheumatic arthritis (RA), MMP inhibitors to be used in these diseases as the indication have not been put on the market. Under such circumstances, attention has been directed toward aggrecanase which selectively degrades aggrecan which is another main constituting component of joint cartilage.

A joint disease-related role of an enzyme aggrecanase which cleaves aggrecan at the site between $Glu^{373}$-$Ala^{374}$ has been revealed by the reports of Sandy et al. and Lohmander et al. stating that all of the main digested aggrecan fragments found in the synovial fluid of human arthritis patients were generated by cleaving at the aggrecanase digestion site (Sandy J. D. et al., *J. Clin. Invest.*, 89, 1512–1516, 1992; Lohmander L. S. et al., *Arthritis Rheum.*, 36, 1214–1222, 1993). On the other hand, it has been known that, in an in vitro explant culture system of joint cartilage, degradation of aggrecan firstly occurs by IL-1 induction and then degradation of type II collagen is accelerated (Dingle L. T. et al., *Ann. Rheum. Dis.*, 34, 303–311, 1975; Cawston T. E. et al., *Biochem. Biophys. Res. Comm.*, 215, 377–385, 1995; Kozaci L. D. et al., *Arthritis Rheum.*, 40, 164–174, 1997). It has been reported that the aggrecan degradation takes the precedence of the type II collagen degradation in a mouse arthritis model too (van Meurs J. B. et al., *Arthritis Rheum.*, 42, 1128–1139, 1999). These reports suggest a possibility that the type II collagen degradation can be controlled by inhibiting the preceding aggrecan degradation.

However, the entity of the aggrecanase which causes joint diseases ("joint disease aggrecanase") has been unclear for long time, though its biochemical properties had been elucidated, namely it is a metalloprotease, it exists in outside of cells, a glycosaminoglycan side chain is concerned in its substrate recognition, its activity is induced by IL-1, TNF and retinoic acid, and the like. Recently, ADAMTS4 (aggrecanase-1: Tortorella M. D. et al., Science, 284, 1664–1666, 1999) and ADAMTS11 (aggrecanase-2: Abbaszade I. et al., *J. Biol. Chem.*, 274, 23443–23450, 1999) have been reported as proteases having an aggrecanase activity. However, it was revealed that they are not the "joint disease aggrecanase", because their gene expression in human OA cartilage is not increased, and their gene expression in an in vitro explant culture system of human knee joint cartilage is not induced by IL-1, TNF and retinoic acid which induce the aggrecanase activity that causes joint diseases (Flannery C. R. et al., *Biochem. Biophys. Res. Commun.*, 260, 318–322, 1999). As described above, the "joint disease aggrecanase" has not been obtained.

DISCLOSURE OF THE INVENTION

Under such circumstances, the present inventors have conducted intensive studies and, as a result, succeeded in isolating a gene coding for a novel metalloprotease having the aggrecanase activity, which is the "joint disease aggrecanase", determining its full-length ORF sequence and thereby achieved production of a recombinant protein.

Also, a vector comprising this gene, a host cell comprising this vector and a method for producing the novel protein using this host cell were established.

Also, the inventors have succeeded in providing a screening method which uses this protein and found that a compound selected by carrying out this screening method significantly inhibits the "aggrecanase activity" (namely, the activity of this protein to cleave the extracellular substrate aggrecan selectively at the site between $Glu^{373}$-$Ala^{374}$) and can become a medicament useful in preventing and/or treating joint diseases.

In addition, a promoter gene of the protein, which is useful in screening a medicament for preventing and/or treating joint diseases was isolated, resulting in accomplishment of the present invention.

Accordingly, the invention relates to:

[1] a metalloprotease having an aggrecanase activity, which comprises an amino acid sequence of from the 213th position to the 583rd position of the amino acid sequence represented by SEQ ID NO:1, or an equivalent of the metalloprotease,

[2] a metalloprotease having an aggrecanase activity, which comprises an amino acid sequence of from the 1st position to the 583rd position of the amino acid sequence represented by SEQ ID NO:1, or an equivalent of the metalloprotease,

[3] a metalloprotease having an aggrecanase activity, which consists of the amino acid sequence represented by SEQ ID NO:1, an amino acid sequence of from the 1st position to the 687th position of the amino acid sequence represented by SEQ ID NO:1, an amino acid sequence of from the 1st position to the 583rd position of the amino acid sequence represented by SEQ ID NO:1, an amino acid sequence of from the 213th position to the 950th position of the amino acid sequence represented by SEQ ID NO:1, an amino acid sequence of from the 213th position to the 687th position of the amino acid sequence represented by SEQ ID NO:1 or an amino acid sequence of from the 213th position to the 583rd position of the amino acid sequence represented by SEQ ID NO:1, or an equivalent of the metalloprotease,

[4] a gene which encodes the metalloprotease having an aggrecanase activity described in any one of [1] to [3] or an amino acid sequence of an equivalent of the metalloprotease,

[5] a vector which comprises the gene described in [4],

[6] a host cell which comprises the vector described in [5],

[7] a method for producing the metalloprotease having an aggrecanase activity described in any one of [1] to [3] or an equivalent of the metalloprotease, which comprises using the host cell described in [6],

[8] an antibody against the metalloprotease having an aggrecanase activity described in any one of [1] to [3] or an equivalent of the metalloprotease,

[9] a method for screening a substance capable of inhibiting an aggrecanase activity of the metalloprotease, which comprises allowing the metalloprotease having an aggrecanase activity described in any one of [1] to [3] or an equivalent of the metalloprotease to contact with a compound to be tested,

[10] a pharmaceutical composition for inhibiting degradation of proteoglycans, which comprises a substance capable of inhibiting the metalloprotease having an aggrecanase activity described in any one of [1] to [3] or an equivalent of the metalloprotease, as an active ingredient, and

[11] a gene represented by SEQ ID NO:24, 25, 26, 27, 28, 29, 30 or 31, or an equivalent of the gene.

The invention also relates to the use of a substance capable of inhibiting an aggrecanase activity of the metalloprotease having an aggrecanase activity described in any one of [1] to [3] or of an equivalent of the metalloprotease, in producing a medicament for inhibiting degradation of proteoglycans.

The invention also relates to the use of a substance capable of inhibiting the metalloprotease having an aggrecanase activity or an equivalent of the metalloprotease, which is obtainable by the screening method described in [9], in treating joint diseases.

The invention also relates to a method for screening a substance capable of modifying a promoter activity of the gene described in [11], which uses this gene.

MODE FOR CARRYING OUT THE INVENTION

The following describes the terms used in the invention. The term "aggrecanase" as used herein means a metalloprotease which has a zinc binding consensus sequence (HExxH) and also has an activity to cleave aggrecan existing in joint cartilage selectively at the site between $Glu^{373}$-$Ala^{374}$, namely the "aggrecanase activity". Also, unless otherwise noted, the "aggrecanase" is referred to as "protein".

The "joint disease aggrecanase" of the invention is any of a metalloprotease having an aggrecanase activity, which comprises an amino acid sequence of from the 213th position to the 583rd position of the amino acid sequence represented by SEQ ID NO:1, or an equivalent of the metalloprotease.

Also, the "joint disease aggrecanase" of the invention is preferably a metalloprotease having an aggrecanase activity, which comprises an amino acid sequence of from the 1st position to the 583rd position of the amino acid sequence represented by SEQ ID NO:1, or an equivalent of the metalloprotease.

More preferably, it is a metalloprotease having an aggrecanase activity, which consists of the amino acid sequence represented by SEQ ID NO:1, an amino acid sequence of from the 1st position to the 687th position of the amino acid sequence represented by SEQ ID NO:1, an amino acid sequence of from the 1st position to the 583rd position of the amino acid sequence represented by SEQ ID NO:1, an amino acid sequence of from the 213th position to the 950th position of the amino acid sequence represented by SEQ ID NO:1, an amino acid sequence of from the 213th position to the 687th position of the amino acid sequence represented by SEQ ID NO:1 or an amino acid sequence of from the 213th position to the 583rd position of the amino acid sequence represented by SEQ ID NO:1, or an equivalent of the metalloprotease.

Regarding the "equivalent of the metalloprotease", (1) in the case of an equivalent of the metalloprotease comprising an amino acid sequence of from the 213th position to the 583rd position of the amino acid sequence represented by SEQ ID NO:1, it is a metalloprotease in which one to several amino acid residues (preferably from 1 to 10, more preferably from 1 to 5) are substituted, deleted and/or inserted at one to several positions (preferably from 1 to 10, more preferably from 1 to 5) in the amino acid sequence of from the 213th position to the 583rd position, and which has the aggrecanase activity, (2) in the case of an equivalent of the metalloprotease comprising an amino acid sequence of from the 1st position to the 583rd position of the amino acid sequence represented by SEQ ID NO:1, it is a metalloprotease in which one to several amino acid residues (preferably from 1 to 10, more preferably from 1 to 5) are substituted, deleted and/or inserted at one to several positions (preferably from 1 to 10, more preferably from 1 to 5) in the amino acid sequence of from the 1st position to the 583rd position, and which has the aggrecanase activity, or (3) in the case of an equivalent of the metalloprotease consisting of the amino acid sequence represented by SEQ ID NO:1, an amino acid sequence of from the 1st position to the 687th position of the amino acid sequence represented by SEQ ID NO:1, an amino acid sequence of from the 1st position to the 583rd position of the amino acid sequence represented by SEQ ID NO:1, an amino acid sequence of from the 213th position to the 950th position of the amino acid sequence represented by SEQ ID NO:1, an amino acid sequence of from the 213th position to the 687th position of the amino acid sequence represented by SEQ ID NO:1 or an amino acid sequence of from the 213th position to the 583rd position of the amino acid sequence represented by SEQ ID NO:1, it is a metalloprotease in which one to several amino acid residues (preferably from 1 to 10, more preferably from 1 to 5) are substituted, deleted and/or inserted at one to several positions (preferably from 1 to 10, more preferably from 1 to 5) in respective sequences, and which has the aggrecanase activity.

Origin of the "joint disease aggrecanase" of the invention is not limited to human. For example, it includes a metalloprotease having the aggrecanase activity which is originated from an organism other than human (e.g., mouse, rat, hamster and dog) and cause joint diseases. Also included is a protein artificially modified by a genetic engineering means based on the sequence of "joint disease aggrecanase" described in SEQ ID NO:1.

Also, the gene coding for the "joint disease aggrecanase" of the invention is any gene which encodes the "joint disease aggrecanase", namely a gene which encodes a metalloprotease having an aggrecanase activity, which comprises an amino acid sequence of from the 213th position to the 583rd position of the amino acid sequence represented by SEQ ID NO:1, or an equivalent of the metalloprotease.

Also, the gene coding for the "joint disease aggrecanase" of the invention may be any gene coding for a metalloprotease having an aggrecanase activity, which comprises an amino acid sequence of from the 1st position to the 583rd position of the amino acid sequence represented by SEQ ID NO:1, or an equivalent of the metalloprotease.

In addition, it may be any gene coding for a metalloprotease having an aggrecanase activity, which consists of the amino acid sequence represented by SEQ ID NO:1, an amino acid sequence of from the 1st position to the 687th position of the amino acid sequence represented by SEQ ID NO:1, an amino acid sequence of from the 1st position to the 583rd position of the amino acid sequence represented by SEQ ID NO:1, an amino acid sequence of from the 213th position to the 950th position of the amino acid sequence represented by SEQ ID NO:1, an amino acid sequence of from the 213th position to the 687th position of the amino acid sequence represented by SEQ ID NO:1 or an amino acid sequence of from the 213th position to the 583rd position of the amino acid sequence represented by SEQ ID NO:1, or an equivalent of the metalloprotease.

Regarding the "gene coding for an equivalent of the metalloprotease", (1) in the case of a gene coding for an equivalent of the metalloprotease comprising an amino acid sequence of from the 213th position to the 583rd position of the amino acid sequence represented by SEQ ID NO:1, it is a gene coding for a metalloprotease in which one to several amino acid residues (preferably from 1 to 10, more preferably from 1 to 5) are substituted, deleted and/or inserted at one to several positions (preferably from 1 to 10, more preferably from 1 to 5) in the amino acid sequence of from the 213th position to the 583rd position, and which has the aggrecanase activity, (2) in the case of a gene coding for an equivalent of the metalloprotease comprising an amino acid sequence of from the 1st position to the 583rd position of the amino acid sequence represented by SEQ ID NO:1, it is a gene coding for a metalloprotease in which one to several amino acid residues (preferably from 1 to 10, more preferably from 1 to 5) are substituted, deleted and/or inserted at one to several positions (preferably from 1 to 10, more preferably from 1 to 5) in the amino acid sequence of from the 1st position to the 583rd position, and which has the aggrecanase activity, or (3) in the case of a gene coding for an equivalent of the metalloprotease consisting of the amino acid sequence represented by SEQ ID NO:1, an amino acid sequence of from the 1st position to the 687th position of the amino acid sequence represented by SEQ ID NO:1, an amino acid sequence of from the 1st position to the 583rd position of the amino acid sequence represented by SEQ ID NO:1, an amino acid sequence of from the 213th position to the 950th position of the amino acid sequence represented by SEQ ID NO:1, an amino acid sequence of from the 213th position to the 687th position of the amino acid sequence represented by SEQ ID NO:1 or an amino acid sequence of from the 213th position to the 583rd position of the amino acid sequence represented by SEQ ID NO:1, it is a gene coding for a metalloprotease in which one to several amino acid residues (preferably from 1 to 10, more preferably from 1 to 5) are substituted, deleted and/or inserted at one to several positions (preferably from 1 to 10, more preferably from 1 to 5) in respective sequences, and which has the aggrecanase activity.

The gene coding for the "joint disease aggrecanase" of the invention is preferably a gene consisting from the 1st position to the 1749th position, from the 1st position to the 2061st position, from the 1st position to the 2850th position, from the 637th position to the 1749th position, from the 637th position to the 2061st position or from the 637th position to the 2850th position, of the nucleotide sequence described in SEQ ID NO:2, more preferably a gene consisting from the 637th position to the 1749th position, from the 637th position to the 2061st position or from the 637th position to the 2850th position, of the nucleotide sequence described in SEQ ID NO:2.

The promoter gene of the invention is preferably a gene having a nucleotide sequence described in SEQ ID NO:24, 25, 26, 27, 28, 29, 30 or 31. The "equivalent of the gene described in SEQ ID NO:24, 25, 26, 27, 28, 29, 30 or 31" is a gene in which one to several bases (preferably from 1 to 10, more preferably from 1 to 5) are substituted, deleted and/or inserted at one to several positions (preferably from 1 to 10, more preferably from 1 to 5) in the nucleotide sequence described in SEQ ID NO:24, 25, 26, 27, 28, 29, 30 or 31, and which has a "joint disease aggrecanase" promoter activity. The term "promoter activity" means an activity which acts as the initiation region for transcribing information of DNA chains to RNA chains.

According to a result of BLAST (basic local alignment search tool) (S. F. Altschul et al., (1990), *J. Mol. Biol.*, 215, 403–410) retrieving of GENBANK and SwissProt, the amino acid sequence (SEQ ID NO:1) (950 amino acids) of MDTS6 as one of the "joint disease aggrecanase" of the invention and the nucleotide sequence (SEQ ID NO:2) (2853 base pairs) which encodes this amino acid sequence are novel. When homology of the amino acid sequence with the ADAMTS4 and ADAMTS11 described in the foregoing was examined, its sequence similarity was 50% or less.

A metalloprotease having an aggrecanase activity, which has high homology with the metalloprotease having the amino acid sequence represented by SEQ ID NO:1, is also included in the "joint disease aggrecanase" of the invention. The high homology metalloprotease having an aggrecanase activity is a metalloprotease having an aggrecanase activity which shows at least 70% or more, preferably 80% or more, more preferably 90% or more, most preferably 95% or more, particularly preferably 99% or more, of sequence homology with the amino acid sequence represented by SEQ ID NO:1. The homology can be specified using the aforementioned BLAST retrieving algorithm.

In addition, the "joint disease aggrecanase" of the invention can be used for the screening of a substance which inhibits the aggrecanase activity that causes joint diseases. The substance which inhibits the aggrecanase activity is useful as a composition for inhibiting degradation of proteoglycans.

In addition, the promoter gene of the "joint disease aggrecanase" of the invention is worthy of notice in that it can be used for the screening of a substance which inhibits the promoter activity. The term "a substance which inhibits the promoter activity" as used herein means a substance which inhibits expression of the "joint disease aggrecanase" by inhibiting action of the promoter. A method for screening a substance capable of inhibiting promoter activity, which uses the promoter gene of the aggrecanase, and use of the substance capable of inhibiting the promoter activity for preventing and/or treating joint diseases are also included in the invention. Furthermore, the "joint disease aggrecanase" promoter gene exists in two or more mutant forms, namely genetic polymorphism. Thus, it can be used for the analysis of correlation between the genetic plymorphism and diseases in which concern of the aggrecanase is considered so that, including joint diseases, as a result, there is a possibility that it can be used as a marker for gene diagnosis.

Regarding the gene coding for the "joint disease aggrecanase" of the invention, the vector of the invention, the host cell of the invention, the method of the invention for producing the "joint disease aggrecanase", the method of the invention for detecting the aggrecanase activity of the "joint disease aggrecanase", the method of the invention for producing an antibody which reacts with the "joint disease aggrecanase", the method of the invention for screening a substance which inhibits the aggrecanase activity of the "joint disease aggrecanase", the method of the invention for detecting the promoter activity and the method of the invention for screening a substance which modifies the promoter activity are described in the following items 1) to 7). All of the items described in 1) to 7) are included in the invention. In the following items 1) to 7), the "joint disease aggrecanase" is described as "protein".

1) Production method of protein gene a) First production method—a method which uses PCR A mRNA sample is extracted from a human cell or tissue having the ability to produce the novel protein of the invention. Next, using this mRNA as the template, two primers interposing the mRNA or a part of mRNA of the novel protein are prepared. Full-length cDNA or a part thereof corresponding to the novel protein can be obtained by modifying denature temperature, denaturing agent adding condition and the like and carrying out a reverse transcriptase-polymerase chain reaction (to be referred to as RT-PCR hereinafter) suited for a respective protein comprising a part of the amino acid sequence represented by SEQ ID NO:1 of the invention. Alternatively, full-length cDNA or a part thereof corresponding to the novel protein can be obtained by carrying out a polymerase chain reaction (to be referred to as RT-PCR hereinafter), by using cDNA prepared using reverse transcriptase from mRNA which is extracted from a human cell or tissue having the ability to produce the novel protein of the invention, or a commercially available cDNA preparation derived from a human cell or tissue, as the template. Thereafter, the novel protein can be produced by integrating the thus obtained full-length cDNA or a part thereof corresponding to the novel protein into an appropriate expression vector and expressing it in a host cell.

Firstly, mRNA comprising a sequence coding for the protease is extracted from a human cell or tissue having the ability to produce the novel protein of the invention by a known method. As the extraction method, a guanidine thiocyanate hot phenol method, a guanidine thiocyanate-guanidine hydrochloride method and the like can be exemplified, but a guanidine thiocyanate cesium chloride method can be preferably cited. The cell or tissue having the ability to produce this protease can be specified by, e.g., northern blot technique using a gene or a part thereof having a nucleotide sequence coding for the protease or western blot technique using an antibody specific for the protease.

Purification of mRNA can be carried out in accordance with a usual method, for example, it can be purified by binding it to an oligo(dT) cellulose column and then eluting it. Alternatively, a commercially available extracted and purified mRNA may be used without extracting the mRNA.

Subsequently, single-strand cDNA is synthesized by carrying out reverse transcriptase reaction of the purified mRNA in the presence of random primers, oligo(dT) primers or custom-synthesized primers. Using two primers interposing a part of the gene of interest, the thus obtained single-strand cDNA is subjected to PCR to amplify the novel protein DNA of interest. Alternatively, a commercially available cDNA preparation may be used without synthesizing the cDNA. The thus obtained DNA is fractionated by a means such as agarose gel electrophoresis or the like. If desired, a DNA fragment of interest can be obtained by digesting this DNA with restriction enzymes and the like and then ligating the digested fragments.

b) Second production method

In addition to the above production method, the gene of the invention can be produced using conventional genetic engineering techniques. Firstly, single-strand cDNA is synthesized using reverse transcriptase and using the mRNA obtained by the above method as the template and then double-strand cDNA is synthesized from this single-strand cDNA. As the method, the S1 nuclease method (Efstratiadis, A. et al., Cell, 7, 279–288, 1976), Land method (Land, H. et al., Nucleic Acids Res., 9, 2251–2266, 1981), O. Joon Yoo method (Yoo, O. J. et al., Proc. Natl. Acad. Sci. USA, 79, 1049–1053, 1983), the Okayama-Berg method (Okayama, H. and Berg, P., Mol. Cell. Biol., 2, 161–170, 1982) and the like can be exemplified.

Next, an *Escherichia coli* strain such as DH5 a strain, HB101 strain, JM109 strain or the like is transformed by introducing a recombinant plasmid obtained by the aforementioned method, and a resulting recombinant can be selected using the resistance for a drug such as tetracycline, ampicillin, kanamycin or the like as a marker. Transformation of a host cell, for example, when the host cell is *E. coli*, can be carried out by Hanahan's method (Hanahan, D. J., Mol. Biol., 166, 557–580, 1983), namely, by adding the recombinant DNA to competent cells prepared in the coexistence of $CaCl_2$ and $MgCl_2$ or RbCl. As a matter of course, commercially available competent cells can also be used. In this connection, in addition to a plasmid, a phage vector such as a lambda system can also be used as a vector.

Regarding the method for selecting DNA of the novel protein of interest from the thus obtained transformants, various methods shown below can for example be employed.

(i) A screening method which uses a synthetic oligonucleotide probe

An oligonucleotide corresponding to whole or a part of the novel protein of the invention is synthesized (in this case, it may be either a nucleotide sequence derived by using the codon usage or a combination of two or more possible nucleotide sequences, and in the latter case, the number of their kinds can be reduced by including inosine), this is hybridized as a probe (after labeling with $^{32}P$ or $^{33}P$) with a nitrocellulose filter or nylon filter on which DNA samples of the transformants are denatured and immobilized, and then the thus obtained positive strains are screened and selected.

(ii) A screening method which uses a probe prepared by polymerase chain reaction Oligonucleotides of a sense primer and an antisense primer corresponding to a part of the novel protein of the invention are synthesized and polymerase chain reaction (Saiki, R. K. et al., Science, 239, 487–491, 1988) is carried out using these primers, thereby effecting amplification of a DNA fragment coding for whole or a part of the novel protein of interest. As the template DNA to be used, cDNA synthesized by reverse transcription reaction from mRNA of cells producing the novel protein or genomic DNA can be used. The thus prepared DNA fragment is labeled with $^{32}P$ or $^{33}P$ and used as the probe to carry out colony hybridization or plaque hybridization to select the clone of interest.

(iii) A screening method in which the novel protein is produced by other animal cells A transformant is cultured to amplify a gene, an animal cell is transfected with the gene (in this case, the vector may be either an autonomously replicating plasmid comprising a transcription promoter region or a plasmid which can be integrated into chromosome of the animal cell), and the protein encoded by the gene is produced in the extracellular moiety. By detecting the novel protein using an antibody specific for the novel protein of the invention, a strain comprising cDNA which encodes the novel protein of interest is selected from the original transformants.

(iv) A selection method which uses an antibody specific for the novel protein of the invention By integrating cDNA into an expression vector in advance, proteins are produced in culture supernatants, inside the cells or on the surface of cells of transformants, and the strain of interest is selected by detecting the novel protein producing strain of interest using an antibody specific for the novel protein of the invention and a secondary antibody against this antibody.

(v) A method which uses a selective hybridization-translation system

Samples of cDNA obtained from transformants are blotted on a nitrocellulose filter or the like, mRNA prepared from the novel protein producing cells of the invention is hybridized therewith, and then the mRNA hybridized to the cDNA is dissociated and recovered. The thus recovered mRNA samples are translated into proteins in a protein translation system, e.g., a system in which they are injected into oocyte of Xenopus or a cell free system such as rabbit reticulocyte lysate, wheat germ or the like. The strain of interest is selected by detecting it using an antibody against the novel protein of the invention.

The method for collecting DNA coding for the novel protein of the invention from the thus obtained transformant of interest can be carried out in accordance with gene manipulation experiment manuals such as of a known method (Sambrook, J. et al., "*Molecular Cloning—A Laboratory Manual*", Cold Spring Harbor Laboratory, NY, 1989) and the like. For example, it can be achieved by separating a fraction corresponding to plasmid DNA from cells and then cutting out the cDNA region from the plasmid DNA.

c) Third production method

The novel protein gene of the invention can also be produced by connecting DNA fragments produced by a chemical synthesis method. Each DNA can be synthesized using a DNA synthesizing machine [e.g., Oligo 1000 M DNA Synthesizer (mfd. by Beckman), 394 DNA/RNA Synthesizer (mfd. by Applied Biosystems) or the like].

d) Fourth production method

The novel protein gene of the invention can also be produced based on the information on the novel protein, for example, by chemical synthesis of nucleic acids in accordance with a conventional method such as phosphite triester method (Hunkapiller, M. et al., *Nature*, 10, 105–111, 1984) or the like. In this connection, codons for desired amino acids are well known, can be selected optionally and can be determined in accordance with a conventional method (Crantham, R. et al., *Nucleic Acids Res.*, 9, r43–r74, 1981), taking codon usage of the host to be used into consideration. In addition, partial modification of codons of these nucleotide sequences can be carried out in the usual way in accordance with the site specific mutagenesis (Mark, D. F. et al., Proc. Natl. Acad. Sci. USA, 81, 5662–5666, 1984) or the like which uses primers comprised of synthetic oligonucleotides which encode the desired modification.

Determination of sequences of DNA obtained by the above methods a) to d) can be carried out for example by Maxam-Gilbert chemical modification method (Maxam, A. M. and Gilbert, W., "Methods in Enzymology", 65, 499–559, 1980), dideoxy nucleotide chain termination method (Messing, J. and Vieira, J., Gene, 19, 269–276, 1982) and the like.

2) Methods for the production of the vector of the invention, the host cell of the invention and the recombinant protein of the invention The thus isolated fragment containing the gene coding for the novel protein of the invention can be transformed into eucaryotic or procaryotic host cells by again integrating it into an appropriate vector DNA. In addition, it is possible to express the gene in respective host cells by introducing an appropriate promoter and a sequence concerned in the gene expression into these vectors.

For example, the eucaryotic host cells include cells of a vertebrate, an insect, yeast and the like, and COS cell as a monkey cell (Gluzman, Y., *Cell*, 23, 175–182, 1081), a dihydrofolate reductase deficient strain of Chinese hamster ovary cell (CHO) (Urlaub, G. and Chasin, L. A., *Proc. Natl. Acad. Sci. USA*, 77, 4216–4220, 1980), human fetal kidney-derived HEK293 cell, 293-EBNA cell in which Epstein-Barr virus EBNA-1 gene is introduced into the same cell (mfd. by Invitrogen) and the like are frequently used as the vertebrate cells, though limited thereto.

As the expression vector for vertebrate cells, a vector having a promoter, a RNA splicing site, a polyadenylylation site, a transcription termination sequence and the like generally positioned upstream of the gene to be expressed can be used, and it may further have a replication origin as occasion demands. Examples of the expression vector include pSV2dhfr having SV40 early promoter (Subramani, S. et al., *Mol. Cell. Biol.*, 1, 854–864, 1981), pEF-BOS having human elongation factor promoter (Mizushima, S. and Nagata, S., *Nucleic Acids Res.*, 18, 5322, 1990), pCEP4 having cytomegalovirus promoter (mfd. by Invitrogen) and the like, though not limited thereto.

In the case of the use of COS cell as the host cell, an expression vector which has SV40 replication origin, can perform autonomous replication in COS cell and has a transcription promoter, a transcription termination signal and an RNA splicing site can be used, and its examples include pME18S (Maruyams, K. and Takebe, Y., *Med. Immunol.*, 20, 27–32, 1990), pEF-BOS (Mizushima, S. and Nagata, S., *Nucleic Acids Res.*, 18, 5322, 1990), pCDM8 (Seed, B., Nature, 329, 840–842, 1987) and the like. The expression vector can be incorporated into COS cell by a DEAE-dextran method (Luthman, H. and Magnusson, G., *Nucleic Acids Res.*, 11, 1295–1308, 1983), a calcium phosphate-DNA co-precipitation method (Graham, F. L. and van der Ed, A. J., Virology, 52, 456–457, 1973), a method which uses FuGENE™6 Transfection Reagent (mfd. by Boehringer Mannheim) , an electroporation method (Neumann, E. et al., *EMBO J.*, 1, 841–845, 1982) and the like, thus enabling to obtain a desired transformant cell.

Also, when CHO cell is used as the host cell, a transformant cell which can stably produce the novel protein can be obtained by co-transfecting a vector capable of expressing neo gene which functions as a G418 resistance marker, such as pRSVneo (Sambrook, J. et al., "Molecular Cloning—A Laboratory Manual", Cold Spring Harbor Laboratory, NY, 1989), pSV2-neo (Southern, P. J. and Berg, P., *J. Mol. Appl. Genet.*, 1, 327–341, 1982) or the like, together with an expression vector and then selecting a G418-resistant colony. Also, when 293-EBNA cell is used as the host cell, a desired transformant cell can be obtained using an expression vector which has Epstein-Barr virus replication origin and can perform autonomous replication in the 293-EBNA cell, such as pCEP4 (mfd. by Invitrogen) or the like.

The thus obtained transformant cell of interest can be cultured in accordance with a conventional method, and the novel protein of the invention is produced in extracellular moiety by this culturing. As the medium to be used in the culturing, various conventionally used media can be optionally selected depending on the host cell employed. In the case of, for example, the COS cell, a medium such as a RPMI-1640 medium, Dulbecco's modified Eagle's minimum essential medium (DMEM) or the like which may be supplemented, as occasion demands, with a serum component such as fetal bovine serum (FBS) or the like may be used. Also, in the case of the 293-EBNA cell, a medium such as Dulbecco's modified Eagle's minimum essential medium (DMEM) or the like supplemented with a serum component such as fetal bovine serum (FBS) or the like and further supplemented with G418 may be used.

The novel protein of the invention thus produced in the extracellular moiety of the transformant cell can be separated and purified by various known separation techniques making use of physical characteristics, biochemical characteristics and the like of the novel protein. Illustrative examples of such techniques include treatment of a culture broth containing the novel protein with a usual protein precipitant, ultrafiltration, various types of liquid chromatography such as molecular sieve chromatography (gel filtration), adsorption chromatography, ion exchange chromatography, affinity chromatography, high performance liquid chromatography (HPLC) and the like, dialysis and combinations thereof.

When the novel protein of the invention is expressed after its in frame fusion with a marker sequence, expression verification, purification and the like of the novel protein become possible. Examples of the marker sequence include FLAG epitope, Hexa-Histidine tag, Hemagglutinin tag, myc epitope and the like. Also, when a specific amino acid sequence recognizable by proteases such as enterokinase, factor Xa, thrombin and the like is inserted between a marker sequence and the novel protein, the marker sequence moiety can be cut off and removed by these proteases.

3) Method for detecting the aggrecanase activity of the protein of the invention The aggrecanase activity of the protein of the invention can be detected by mixing the joint disease aggrecanase of the invention with each of the substrates described below in an appropriate buffer solution, allowing them to react with each other and then detecting the reaction product by a method suited for each substrate.

As the substrate, aggrecan purified from a cartilage or tissue of human or other animal, aggrecan obtained by genetic recombination, commercially available aggrecan (mfd. by Seikagaku Kogyo) or a partial protein thereof can be used. The aggrecanase activity can be measured by allowing these substrates to react with a cell or tissue culture broth, a cell or tissue extract or a (partially) purified sample containing a protease to be tested, and then detecting a fragment cleaved off at the site between $Glu^{373}$-$Ala^{374}$. The fragment cleaved off at the site between $Glu^{373}$-$Ala^{374}$ can be detected by a method in which an N-terminal sequence or a C-terminal sequence of the digested fragment is determined in accordance with a conventional method, or more conveniently, by an immunological method such as an ELISA (enzyme-linked inmmunosorbent assay) which uses an anti-neoepitope antibody capable of specifically recognizing C-terminal $NITGE^{373}$ and N-terminal $^{374}ARGSV$ generated by the cutting between $Glu^{373}$-$Ala^{374}$, a western blotting or the like. Preferably, it can be carried out by the methods described in Examples 7 and 9.

4) Method for preparing antibody which reacts with the novel protein of the invention The antibody which reacts with the novel protein of the invention, such as a polyclonal antibody or a monoclonal antibody, can be obtained by directly administering the novel protein or a fragment of the novel protein to various animals. It can also be obtained by a DNA vaccine method (Raz, E. et al., *Proc. Natl. Acad. Sci. USA*, 91, 9519–9523, 1994; Donnelly, J. J. et al., *J. Infect. Dis.*, 173, 314–320, 1996) using a plasmid into which a gene coding for the novel protein of the invention is introduced.

A polyclonal antibody is produced from a serum or egg of an animal such as rabbit, rat, goat, domestic fowl or the like which is sensitized by immunizing the animal with the novel protein or a fragment thereof emulsified in an appropriate adjuvant such as complete Freund's adjuvant by its peritoneal, subcutaneous, intravenous or the like injection. The thus produced polyclonal antibody can be separated and purified by usual protein isolation and purification techniques, and examples of the usual protein isolation and purification techniques include centrifugation, dialysis, salting out with ammonium sulfate and a chromatography using DEAE-cellulose, hydroxyapatite, protein A agarose or the like.

A monoclonal antibody can be produced easily by those skilled in the art by the cell fusion method of Kohler and Milstein (Kohler, G. and Milstein, C., *Nature*, 256, 495–497, 1975).

That is, mouse is immunized by emulsifying the novel protein of the invention or a fragment thereof in an appropriate adjuvant such as complete Freund's adjuvant and inoculating the emulsion several times at intervals of a few weeks by its peritoneal, subcutaneous, intravenous or the like injection. After the final immunization, spleen cells are taken out and fused with myeloma cells to prepare hybridomas.

As the myeloma cells for obtaining hybridomas, a myeloma cell having a marker (e.g., hypoxanthine-guanine phosphoribosyl transferase deletion, thymidine kinase deletion or the like), such as a mouse myeloma cell strain P3X63Ag8.U1, is used. Also, polyethylene glycol is used as the fusing agent. As the medium for preparing hybridomas, Eagle's minimum essential medium, Dulbecco's minimum essential medium, RPMI1640 or the like usually used medium is used by optionally supplementing it with 10 to 30% fetal bovine serum. The fused strains are selected by the HAT selection method. Screening of hybridomas is carried out using culture supernatants by ELISA, immunological tissue staining or the like well known method or by the aforementioned screening method, and a clone of hybridoma which secretes the antibody of interest is selected. Also, monoclonal nature of the hybridoma is confirmed by repeating subcloning by limiting dilution. By culturing the thus obtained hybridoma in a medium for several days or in the abdominal cavity of a pristane-pretreated BALB/c mouse for 10 to 20 days, the antibody is produced in a purification-possible amount. The thus produced monoclonal antibody can be separated and purified from the culture supernatant or ascitic fluid by usual protein isolation purification techniques.

Active antibody fragments containing a part of the antibody, such as F(ab')$_2$, Fab, Fab' and Fv, can be obtained by digesting the thus separated and purified antibody with a proteolytic enzyme such as pepsin, papain or the like in the conventional way and then separating and purifying the fragments by usual protein isolation purification techniques.

Furthermore, it is possible to obtain the antibody which reacts with the novel protein of the invention as single chain Fv or Fab by the methods of Clackson et al. and Zebedee et al. (Clackson, T. et al., *Nature*, 352, 624–628, 1991; Zebedee, S. et al., *Proc. Natl. Acad. Sci. USA*, 89, 3175–3179, 1992). In addition, it is possible to obtain a human antibody by immunizing a transgenic mouse in which a mouse antibody gene is replaced by a human antibody gene (Lonberg, N. et al., *Nature*, 368, 856–859, 1994).

5) Method for screening a substance which inhibits the aggrecanase activity of the "joint disease aggrecanase" of the invention This can be screened by a similar method of the aggrecanase activity detection method described in 3). Also, the ELISA or the like method exemplified in Example 10-2 can be used, in which added aggrecan, recombinant aggrecan, commercially available aggrecan or a partial protein thereof which disappears or decreases by its degradation when allowed to react with the novel protein of the invention is measured using an antibody which specifically recognizes polypeptides of the N-terminal side and C-terminal side moieties of the region cleaved off with aggrecanase. Also useful is a method in which the novel protein of the invention is allowed to react with a recombinant aggrecan in which FLAG tag is added to the N-terminal, and His tag to the C-terminal, as exemplified in Example 7-1, and the added recombinant aggrecan disappeared or decreased by its degradation is measured by ELISA or the like method using an anti-FLAG tag and anti-His tag antibodies. The tags in this case are not limited to FLAG tag and His tag, and the recombinant aggrecan is not limited to Example 7-1 and may be a partial protein or modified protein of aggrecan which is cleaved off at the aggrecanase digesting site by this protein. Regarding the substance to be tested for its aggrecanase activity, compounds or peptides which are generally known to have metalloprotease inhibition activity but their activities to inhibit the aggrecanase activity of the novel protein are unclear, or various known compounds and peptides, compounds synthesized using combinatorial chemistry techniques (Terrett, N. K. et al., *Tetrahedron*, 51, 8135–8137, 1995) or general synthesis techniques and random peptides prepared by applying a phage display method (Felici, F. et al., *J. Mol. Biol.*, 222, 301–310, 1991) and the like, can be used as the substance to be tested. In addition, extracts and culture supernatants of microorganisms, natural components derived from plants and marine organisms, animal tissue extracts and the like are also become objects of the screening. Or possibly, compounds or peptides prepared by chemically or biologically structure-modified from compounds or peptides selected by the screening method of the invention can also be used.

For the screening of substances which inhibit the aggrecanase activity of the novel protein of the invention (compounds, peptides, antibodies and antibody fragments), any substance which becomes the substrate of the novel protein of the invention or of a partial peptide thereof can be used, and the substrates described in the aforementioned item 3) are desirable.

6) Method for detecting degradation and release of proteoglycan

A method exemplified in Example 11-2 in which $^{35}SO_4^{2-}$ is used as a tracer, a method in which a proteoglycan antibody is used, a method in which degraded fragments are detected by gel filtration (Methods in Cartilage Research, Academic Press, 1990; Joint Cartilage Degradation, Marcel Dekker, Inc., 1993), a colorimetric method (Goldberg R. L. and Kolibas L. M., *Connect. Tissue Res.*, 24, 265–275, 1990) which uses 1,9-dimethylmethylene blue (DMMB) and the like are used for the detection and measurement of the degradation and release of cartilage proteoglycan, though not limited thereto.

7) Method for screening a substance which inhibits promoter activity of the invention In screening a substance which inhibits the promoter activity of the invention, a method in which a reporter gene plasmid containing the sequences shown in Example 13 (SEQ ID NOs:24 and 31) and partial sequences thereof is used is convenient as the method for detecting the promoter activity. The reporter gene means a gene coding for a protein which can be determined by usual means (e.g., determination methods well known to those skilled in the art such as measurement of enzyme activities and the like), and chloramphenicol acetyltransferase, luciferase, β-galactosidase and alkaline phosphatase genes are frequently used, though not limited thereto. Regarding a vector for constructing a reporter gene plasmid, there is no limitation and commercially available plasmid vectors such as pGV-B2 (mfd. by Toyo Ink), pSEAP2-Basic (mfd. by Clontech) and the like can be used. By constructing a reporter gene plasmid in which the sequence is inserted in the forward direction into upstream of the reporter gene of these vectors and measuring amount of the reporter protein expressed in cells transformed with this plasmid, by a method suited for respective case, the presence and strength of the promoter activity of the sequence can be known, and action of a substance to be tested upon this promoter activity can be detected by adding the substance to be tested to a culture broth of the transformed cells.

For the screening of substances which inhibit the promoter activity possessed by the sequence of the Sequence ID No. of the invention and a partial sequence thereof (compounds, peptides, antibodies and antibody fragments), a method similar to the aforementioned promoter activity detection method can be used. Regarding the substance to be tested, compounds or peptides which are generally known to have promoter inhibition activity but their activities to inhibit the promoter activity possessed by the sequences of SEQ ID NOs:24 and 31 and partial sequences thereof are unclear or various known compounds and peptides, compounds synthesized using combinatorial chemistry techniques (Terrett, N. K. et al., *Tetrahedron*, 51, 8135–8137, 1995) or general synthesis techniques and random peptides, antibodies and antibody fragments prepared by applying a phage display method (Felici, F. et al., *J. Mol. Biol.*, 222, 301–310, 1991) can be used. In addition, extracts and culture supernatants of microorganisms, natural components derived from plants and marine organisms, animal tissue extracts and the like are also become the object of the screening. Or possibly, compounds or peptides prepared by chemically or biologically structure-modified from compounds or peptides selected by the screening method of the invention can also be used.

A medicament which comprises as the active ingredient a substance which inhibits the aggrecanase activity of the "joint disease aggrecanase" and is selected by the aforementioned screening method (a compound, peptide, antibody or antibody fragment) is included in the invention, and a pharmaceutical composition for inhibiting degradation of proteoglycans is particularly desirable as the medicament. Examples of the substance which significantly inhibits activity of the "joint disease aggrecanase" include $N^{\alpha}$-[2-(1-hydroxycarbamoyl-2-sulfanylethyl)-4-methylpentanoyl]-N,O-dimethyltyrosineamide (to be referred to as compound A hereinafter), $N^{\alpha}$-[$_2$-(1-hydroxycarbamoyl-2-sulfanylethyl)-4-methylpentanoyl]-N-methylphenylalanineamide (to be referred to as compound B hereinafter), $N^{\alpha}$-[2-(1-hydroxycarbamoyl-2-phenylsulfanylethyl)-4-methylpentanoyl]-N,O-dimethyltyrosineamide (to be referred to as compound C hereinafter), $N^{\alpha}$-[2-(1-hydroxycarbamoyl-2-methylsulfanylethyl)-4-methylpentanoyl]-N,O-dimethyltyrosineamide (to be referred to as compound D hereinafter) and the like selected by the screening system shown in Example 10-2. The compound A, compound B, compound C and compound D are compounds included in the claims of WO 90/05719, but not only medicaments comprising these compounds as the active ingredient but also all medicaments which comprises substances capable of significantly inhibiting the aggrecanase activity of the "joint disease aggrecanase" are included in the invention. In this connection, the compound A, compound B, compound C and compound D are compounds can be synthesized in the same manner as the compounds disclosed in WO 90/05719 in accordance with the production methods disclosed in WO 90/05719.

The medicament comprising a substance (a compound, peptide, antibody or antibody fragment) which significantly inhibits the aggrecanase activity of the "joint disease aggrecanase" of the invention as the active ingredient can be prepared using carriers, fillers and other additives usually used for their preparation, in response to each type of the active ingredient.

Examples of its administration include oral administration using tablets, pills, capsules, granules, fine subtilaes, powders, oral solutions and the like and parenteral administration using intravenous, intramuscular, intraarticular and the like injections, suppositories, percutaneous preparations, transmucosal preparations and the like. Particularly in the case of peptides which are digested in the stomach, parenteral administration such as intravenous injection or the like is desirable.

In the solid composition for use in the oral administration according to the present invention, one or more active substances are mixed with at least one inert diluent such as lactose, mannitol, glucose, microcrystalline cellulose, hydroxypropylcellulose, starch, polyvinyl pyrrolidone, aluminum magnesium silicate or the like. In the usual way, the composition may contain other additives than the inert diluent, such as a lubricant, a disintegrating agent, a stabilizing agent, a solubilizing or solubilization assisting agent or the like. If necessary, tablets or pills may be coated with a sugar or a film of a gastric or enteric substance.

The liquid composition for oral administration includes emulsions, solutions, suspensions, syrups and elixirs and contains a generally used inert diluent such as purified water or ethanol. In addition to the inert diluent, this composition may contain auxiliary agents such as a moistening agent, a suspending agent, a sweetener, an aromatic agent and an antiseptic agent.

The injections for parenteral administration includes aseptic aqueous or non-aqueous solutions, suspensions and emulsions. Examples of the diluent for use in the aqueous solutions and suspensions include distilled water for injection, physiological saline and the like. Examples of the diluent for use in the non-aqueous solutions and suspensions include propylene glycol, polyethylene glycol, plant oil (e.g., olive oil or the like), alcohol (e.g., ethanol), Polysorbate 80 and the like. Such a composition may further contain a moistening agent, an emulsifying agent, a dispersing agent, a stabilizing agent, a solubilizing or solubilization assisting agent, an antiseptic and the like. These compositions are sterilized by filtration through a bacteria retaining filter, blending of a germicide or irradiation. Alternatively, they may be used by firstly making into sterile solid compositions and dissolving them in sterile water or a sterile solvent for injection use prior to their use.

The clinical dose is optionally decided by taking into consideration strength of activity of the active ingredient selected by the aforementioned screening method, symptoms, age, sex and the like of each patient to be treated.

For example, the dose is usually from about 0.1 to 1,000 mg, preferably from 0.1 to 100 mg, per day per adult (as 60 kg in body weight) in the case of oral administration. In the case of parenteral administration, it is from about 0.01 to 1,000 mg, preferably from 0.01 to 100 mg, per day in the form of injections.

BEST MODE FOR CARRYING OUT THE INVENTION

Figure 1:
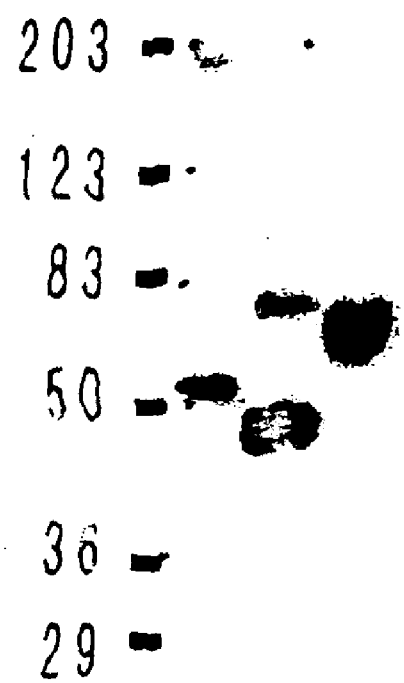
FIG. 1 is a photograph showing a result of the expression of MDTS6TSP1 in an animal cell strain using an ECL western blotting detection system, obtained in Example 6.

The following describes the invention more illustratively.

Unless otherwise noted, experiments were carried out in accordance with gene manipulation experiment manuals such as of a known method (Sambrook, J. et al., "Molecular Cloning—A Laboratory Manual", Cold Spring Harbor Laboratory, NY, 1989) and the like, but the invention is not limited to the Examples.

EXAMPLE 1

Discovery of Partial Sequence of a Novel ADAMTS Gene MDTS6

A human brain cDNA library strictly fractionated by the size of insertion sequences was constructed as shown in a reference (Ohara O. et al., *DNA Res.*, 4, 53–59, 1997). Size distribution of cDNA fragments in these sub-libraries was from 3 kbp to 8 kbp. By deciphering 5'- and 3'-end sequences of clones constituting this library, an in-house EST data bank was constructed. A partial sequence of MDTS6 was obtained from this.

EXAMPLE 2

Determination of Full-length ORF Sequence of MDTS6

By determining sequences of MDTS6 cDNA clones, a sequence of from the 832nd position to the 2853rd position of SEQ ID NO:2 was obtained. The sequence of from the 1st position to the 831st position of SEQ ID NO:2 was obtained by repeating RACE (Rapid Amplification of cDNA Ends) using human brain and human placenta Marathon-Ready™ cDNA manufactured by Clontech as the template and LA-Taq™ (mfd. by Takara Shuzo) as the DNA polymerase. As a result, it was revealed that the full-length MDTS6 was a novel protein composed of 950 amino acids as shown in SEQ ID NO:1. Its domain structure was composed of a secretion signal sequence, a pro region, a furin protease recognition sequence, a metalloprotease domain, a disintegrin domain, a thrombospondin type I repeat sequence (to be referred to as TSP-1 repeat sequence hereinafter), a domain rich in Cys residue, an intermediate region and two TSP-1 repeat sequences, in order from the N-terminus, and it was a molecule belonging to the ADAMTS family (Kuno, K. et al., *J. Biol. Chem.*, 272, 556–562, 1997; Tang, B. L. et al., *FEBS Lett.*, 445, 223–225, 1999).

EXAMPLE 3

Preparation of C-terminal FLAG Addition Type Expression Vector

An EBNA1 expression unit-removed expression vector pCEP4d was constructed by digesting pCEP4 (mfd. by Invitrogen) with restriction enzymes ClaI and NsiI, blunt-ending the resulting fragments and then carrying out their autonomous ligation. This vector was digested with restriction enzymes NheI and BamHI and extracted from an agarose gel to obtain a fragment of about 7.7 kbp, and a double strand of oligonucleotide obtained by annealing a nucleic acid shown by SEQ ID NO:3 and a nucleic acid shown by SEQ ID NO:4 was inserted into the fragment to select a clone having the planned sequence which was named pCEP4d-FLAG. Using this vector as the template and oligoDNA shown by SEQ ID NO:5 and oligoDNA shown by SEQ ID NO:6 as primers, PCR was carried out using PyroBest™ DNA polymerase. The thus generated DNA fragment of about 0.4 kbp was digested with a restriction enzyme SpeI and inserted into pCEP4d-FLAG (about 7.7 kbp) which had been digested with XbaI, and a clone in which XbaI, NheI, NotI and BamHI recognition sequence cloning sites and FLAG tag were arranged in that order from the promoter as intended was selected, thereby completing pCEP4dE2-FLAG.

EXAMPLE 4

Construction of MDTS6 Truncated Protein (MDTS6TSP1) Expression Plasmid

A plasmid was constructed in the following manner for use in expressing a sequence of from the 1st position to the 583rd position of SEQ ID NO:1 (a moiety corresponding to a region containing the TSP1 repeat sequence from the N-terminus of MDTS6 (to be referred to as MDTS6TSP1 hereinafter)) as a protein in which FLAG was added to the C-terminus.

Firstly, a gene of from the 1st position to the 1749th position of SEQ ID NO:2 was obtained by PCR. Using oligoDNA sequences represented by SEQ ID NO:7 and SEQ ID NO:8 as primers, human placenta Marathon-Ready™ cDNA (mfd. by Clontech) as the template and LA-Taqe™ (mfd. by Takara Shuzo) as DNA polymerase, a cycle of 98° C. for 10 seconds and 68° C. for 2 minutes was repeated 10 times after heating at 94° C. for 1 minutes. Using a DNA solution prepared by 50 times-diluting this reaction solution as the template and using PyroBest™ DNA polymerase, PCR was carried out under a condition of 94° C. for 2 minutes, 40 repetitions of a cycle of 98° C. for 10 seconds, 66° C. for 30 seconds and 74° C. for 4 minutes and subsequent 72° C. for 10 minutes. The thus generated fragment of interest in which XbaI recognition sequence and Kozak sequence were added to the 5' side, and NotI recognition sequence to the 3' side, was subcloned into PCR-Blunt to confirm the sequence and then digested with restriction enzymes XbaI and NotI and inserted into the XbaI-NotI site of pCEP4dE2-FLAG to complete pCEP-MDTS6TSP1-FLAG.

EXAMPLE 5

Construction of MDTS6 Full-length Protein Expression Plasmid

A plasmid was constructed in the following manner for use in expressing a sequence of from the 1st position to the 950th position of SEQ ID NO:1 as a protein in which FLAG was added to the C-terminus.

Firstly, a gene of from the 1534th position to the 2850th position of SEQ ID NO:2 was obtained by PCR. Illustratively, using oligoDNA sequences represented by SEQ ID NO:9 and SEQ ID NO:10 as primers, the plasmid DNA of EST clone as the template and PyroBest™ DNA polymerase as DNA polymerase, a cycle of 98° C. for 10 seconds, 50° C. for 15 seconds and 72° C. for 2 minutes was repeated 20 times after heating at 94° C. for 1 minutes, followed by 7 minutes of reaction at 72° C. In this connection, it was able to generate the fragment of interest by carrying out PCR using human placenta Marathon-Ready™ cDNA (mfd. by Clontech) as the template, instead of using the plasmid DNA of EST clone as the template, and using oligoDNA sequences represented by SEQ ID NO:9 and SEQ ID NO:10 as primers under a condition of 94° C.

for 2 minutes, 40 repetitions of a cycle of 98° C. for 10 seconds and 68° C. for 2 minutes and subsequent 72° C. for 7 minutes. The thus generated fragment of interest in which NotI recognition sequence was added to the 3' side was subcloned into PCR-Blunt to confirm the sequence and used as pCRB-MDTS6-3H.

Making use of the presence of a BamHI recognition sequence in a sequence of from the 1566th position to the 1571st position of SEQ ID NO:2, pCEP-MDTS6TSP1-FLAG was digested with restriction enzymes XbaI and BamHI, and the thus generated DNA fragment of about 1.6 kbp was connected to a DNA fragment of about 1.3 kbp generated by digesting pCRB-MDTS6-3H with BamHI and NotI and inserted into the XbaI-NotI site of pCEP4dE2-FLAG to complete pCEP-MDTS6F-FLAG.

EXAMPLE 6

Expression of MDTS6TSP1 and MDTS6 Full-length Proteins by Animal Cell Strain

The expression plasmid prepared in Example 4 using pCEP4dE2-FLAG as the backbone was introduced into HEK293-EBNA cell (mfd. by Invitrogen) using FuGENE™6 Transfection Reagent (mfd. by Boehringer Mannheim) in accordance with the attached instructions. After introduction of the plasmid, the presence of the protein of interest in a culture supernatant obtained by 1 to 2 days of culturing was confirmed by western blotting using an antibody against FLAG tag added to the C-terminus (a mouse anti-FLAG monoclonal antibody (M2; mfd. by Sigma)). That is, the culture supernatant was subjected to electrophoresis using SDS/10% to 20% acrylamide gel (mfd. by Daiichi Pure Chemicals) and then transferred on a PVDF membrane using a blotting apparatus. The PVDF membrane after the transfer was subjected to blocking by adding Block Ace (mfd. by Dainippon Pharmaceutical) and then allowed to react with the mouse anti-FLAG monoclonal antibody (M2; mfd. by Sigma) and a horseradish peroxidase-labeled rabbit anti-mouse IgG polyclonal antibody (mfd. by Zymed or TAGO) in that order. Alternatively, after the blocking, it was allowed to react with biotinylated M2 antibody (mfd. by Sigma) and a streptoavidine-horseradish peroxidase conjugate (mfd. by Amersham) in that order. After the reaction, expression of the protein was confirmed using an ECL western blotting detection system (mfd. by Amersham Pharmacia) (FIG. 1). Molecular weight of the expressed MDTS6TSP1 protein was smaller than the value calculated from the amino acid sequence by a factor of about 23 K. Making use of the fact that FLAG tag is added to the C-terminus of MDTS6TSP1 protein expressed by the HEK293-EBNA cell as described in the foregoing, MDTS6TSP1 protein was affinity-purified by the method of Example 7-1 and then transferred on a PVDF membrane, and the N-terminal sequence of MDTS6TSP1 protein stained with Ponceau S was determined by analyzing with Type 494 Peptide Sequencer manufactured by ABI. As a result, it was shown that it starts from the 213th position Phe of SEQ ID NO:1 and, similar to the case of other ADAMTS molecules, becomes mature protein (from 213th position to 583rd position of SEQ ID NO:1) by being cleaved at the furin protease recognition sequence existing between the pro region and metalloprotease domain. Also, the MDTS6 full-length protein was obtained in the same manner as the case of the above MDTS6TSP1 protein expression using the expression plasmid obtained in Example 5, and similar to the case of MDTS6TSP1, it was confirmed that it becomes mature protein (from 213th position to 950th position of SEQ ID NO:1) by being cleaved at the furin protease recognition sequence existing between the pro region and metalloprotease domain.

EXAMPLE 7

Detection of Enzyme Activity of MDTS6TSP1 Protein Expressed in Animal Cell Host

EXAMPLE 7-1

Preparation of Recombinant Aggrecan G1G2

Using oligoDNA sequences represented by SEQ ID NO:11 and SEQ ID NO:12 synthesized based on the reported gene sequence of human aggrecan (Doege K. et al., *Biochem. Soc. Trans.*, 18, 200–202, 1990) as primers, human placenta Marathon-Ready™ cDNA as the template and PyroBest™ DNA polymerase as DNA polymerase, the reaction of 94° C. for 1 minute, 40 repetitions of a cycle of 98° C. for 10 seconds and 68° C. for 2 minutes, and subsequent 68° C. for 7 minutes was carried out. The thus generated DNA fragment was digested with a restriction enzyme BamHI and inserted into the BamHI site of pCEP-SigFla, thereby completing an expression plasmid pCEP-rAgg for use in the expression of a protein in which FLAG tag is added to the N-terminus, and His tag to the C-terminus, of the globular domain 1 (G1)-globular domain 2 (G2) of human aggrecan. The pCEP-SigFla is an expression vector which is prepared by introducing double strand of the oligoDNA sequences represented by SEQ ID NO:13 and SEQ ID NO:14 into the HindIII-XhoI site of pCEP4d and has the influenza virus hemagglutinin secretion signal sequence described in the report (Guan X-M. et al., *J. Biol. Chem.*, 267, 21995–21998, 1992), FLAG tag and BamHI recognition sequence in that order downstream of the promoter.

The plasmid pCEP-rAgg was introduced into HEK293-EBNA cell which was subsequently cultured for 3 to 7 days, thereby effecting expression and production of the protein of interest. Purification of the protein of interest from the culture supernatant was carried out by an affinity purification making use of the addition of FLAG tag to the N-terminus. That is, the culture supernatant was applied to M2-agarose (mfd. by Sigma) packed in a column, washed with 20 mM Tris-HCl (pH 7.4)/150 mM NaCl (to be referred to as TBS hereinafter), eluted and fractionated with 0.1 M Gly-HCl (pH 3.0) and immediately neutralized with 1 M Tris-HCl (pH 8.0).

EXAMPLE 7-2

Detection of Recombinant Aggrecan G1G2 Degrading Activity of MDTS6TSP1 Protein

Figure 2:
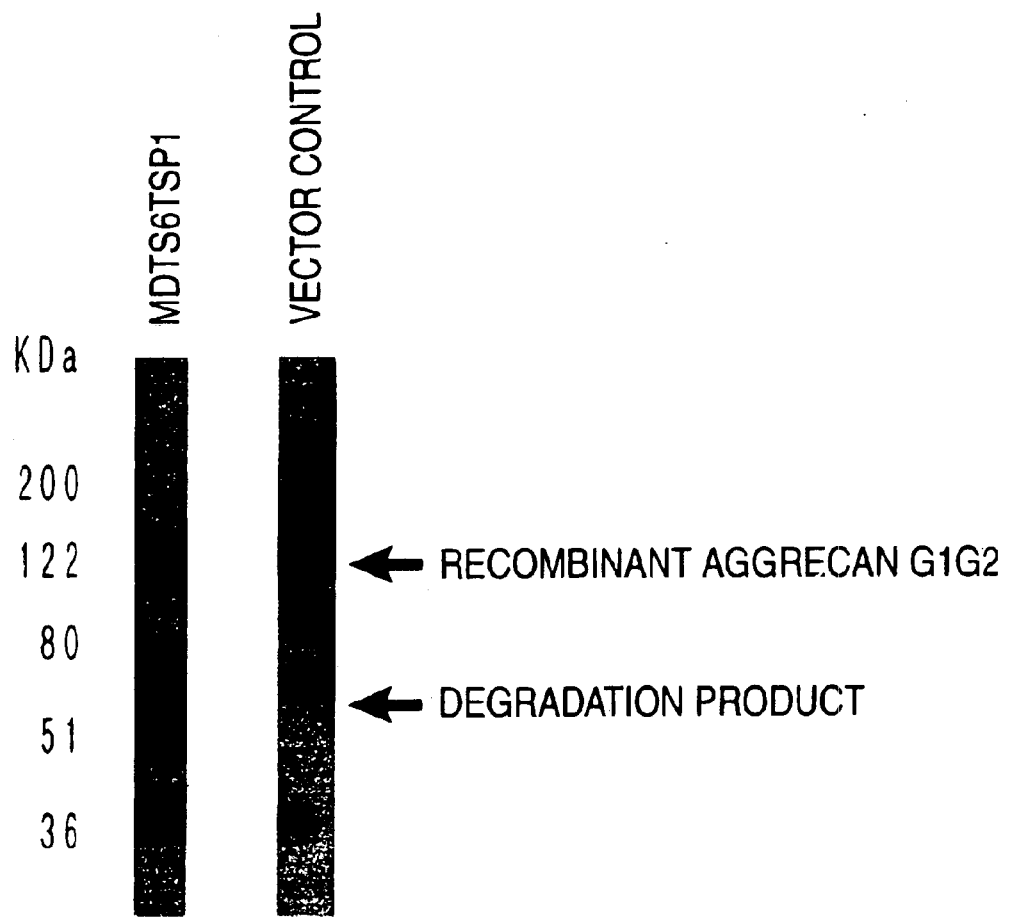
FIG. 2 is a photograph showing a result of the detection of the activity of MDTS6TSP1 to degrade a recombinant aggrecan G1G2 using an ECL western blotting detection system, obtained in Example 7-2.

In Example 6, the medium 12 to 16 hours after introduction of the expression plasmid was replaced by a serum-free medium, and the culturing was continued for 32 to 36 hours to recover the culture supernatant. This culture supernatant was mixed with the recombinant aggrecan prepared in the foregoing, and the mixture was allowed to undergo the reaction at 37° C. overnight, subjected to SDS-PAGE, transferred on a PVDF membrane and blocked by the method described in Example 6 and then allowed to react with an anti-Hisx6 polyclonal antibody (sc-803; mfd. by Santa Cruz Biotechnology) and a horseradish peroxidase-labeled goat anti-rabbit IgG polyclonal antibody (mfd. by BML) in that order. After the reaction, the recombinant aggrecan was detected using an ECL western blotting system (mfd. by Amersham Pharmacia). As a result, degraded fragment of the recombinant aggrecan, which was not found in the control in which only the expression plasmid was introduced, was detected (FIG. 2).

EXAMPLE 7-3

Analysis by Anti-aggrecanase Neoepitope Antibody

Figure 3:
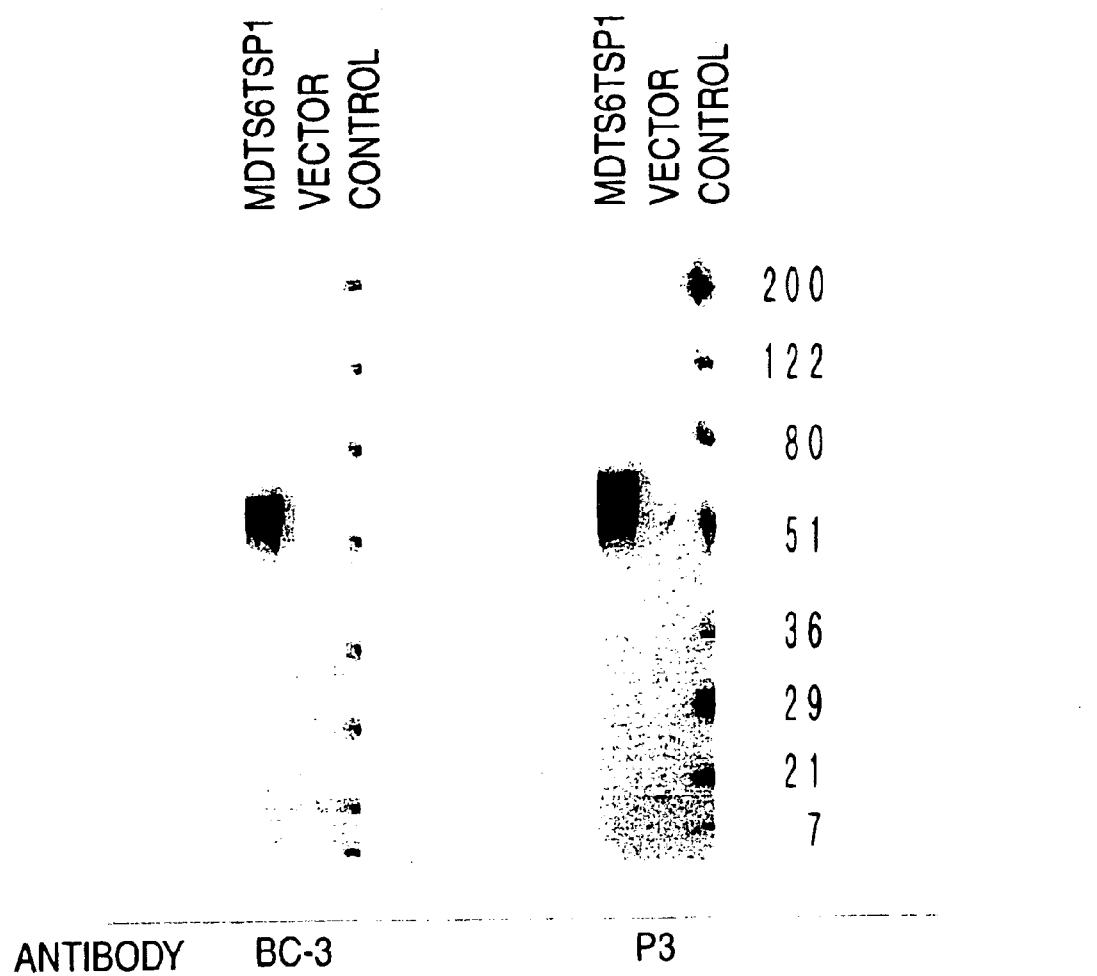
FIG. 3 is a photograph showing a result of the analysts of a recombinant aggrecan G1G2 degraded with MDTS6TSP1, by an anti-aggrecanase neoepitope antibody, using a western blotting detection system, obtained in Example 7-3.

Aggrecanase is a metalloprotease which selectively cleaves aggrecan at the site between $Glu^{373}$-$Ala^{374}$. An antibody capable of recognizing a C-side neoepitope generated by this cleavage was prepared in accordance with a usual method by repeating immunization of mouse with a conjugate of the synthetic peptide represented by SEQ ID NO:32 and KLH, 5 times. A PVDF membrane after transfer and blocking carried out in the same manner as in Example 7-2 was allowed to react with this antibody, allowed to react with a peroxidase-labeled goat anti-mouse IgG polyclonal antibody (mfd. by Tago) and then detected using an ECL western blotting detection system (mfd. by Amersham Pharmacia). As a result, the degraded product of recombinant aggrecan generated by MDTS6 reacted with the anti-aggrecanase neoepitope antibody, and molecular weight of the detected band is consistent with the molecular weight of the degraded product detected in Example 7-2 (FIG. 3). The same result was obtained by the BC-3 antibody which recognizes aggrecanase neoepitope (Hughes C. E. et al., Biochemical J., 305, 799–804, 1995).

EXAMPLE 8

Expression Induction of MDTS6 mRNA by IL-1

Figure 4:
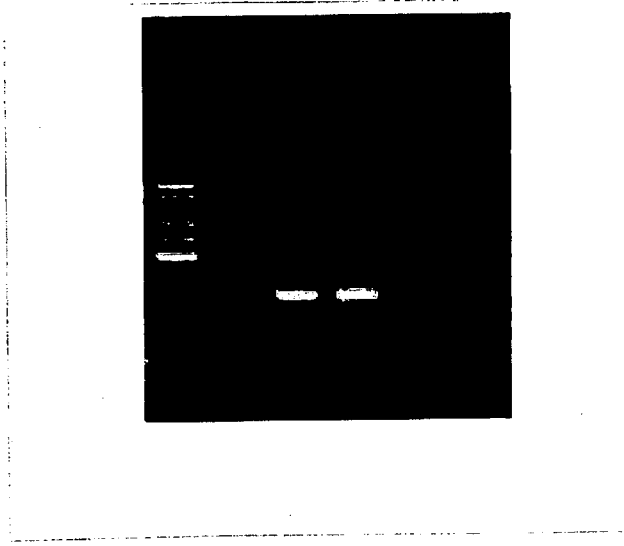
FIG. 4 is an electrophoresis pattern photograph showing a result of the examination of MDTS6 mRNA expression induction by IL-1β, obtained in Example 8.

It is known that a mouse cell strain ATDC5 is differentiated into a chondrocyte-like cell by insulin treatment (Atsumi T. et al., Cell Differ. Dev., 30, 109–116, 1990). The ATDC5 cells were inoculated in $4 \times 10^5$/well portions into an I type collagen-coated 6 well plate (mfd. by Asahi Technoglass) and cultured for 2 days using DMEM/HamF12 (1:1)/5% FCS medium, the medium was changed to DMEM/HamF12 (1:1)/5% FCS medium containing insulin (final concentration 30 ng/ml) and 50 µg/ml of L-ascorbic acid and the culturing was continued for 5 days, and then the resulting cells were treated for 0, 1, 2, 4 or 8 hours by adding IL-1β (final concentration 5 ng/ml). Total RNA was prepared from each of the treated groups using ISOGEN (mfd. by Nippon Gene), and RT-PCR was carried out using 1 µg portion thereof as the template and using BcaBEST™ RNA PCR Kit (mfd. by Takara Shuzo). The reverse transcription reaction was carried out using Oligo dT-Adaptor Primer as the primer in accordance with the attached instructions, and PCR was carried out using oligoDNA sequences represented by SEQ ID NO:15 and SEQ ID NO:16 as primers, which had been synthesized based on the 3' non-translation region of MDTS6, by the reaction of 94° C. for 2 minutes, 40 repetitions of a cycle of 94° C. for 30 seconds, 60° C. for 30 seconds and 72° C. for 30 seconds, and subsequent 72° C. for 7 minutes. The reaction solution was subjected to electrophoresis with 1% agarose, and densities of the thus generated bands of about 0.3 kbp were compared. As a result, it was found that expression of the MDTS6 mRNA is transiently induced by IL-1 (FIG. 4).

EXAMPLE 9

Degradation of Natural Type Aggrecan by MDTS6

EXAMPLE 9-1

Expression of Various Full-length MDTS6 Proteins and Their Recombinant Aggrecan G1G2 Degrading Activity The expression plasmid constructed using pCEP4dE2-FLAG as the backbone was introduced into HEK293-EBNA cell (mfd. by Invitrogen) using FuGENE™6 Transfection Reagent (mfd. by Boehringer Mannheim) in accordance with the attached instructions. After introduction of the plasmid, the resulting cells were cultured overnight and washed with PBS buffer, and then the medium was changed to a serum-free medium and the culturing was continued for 2 to 3 days. The resulting culture broth was centrifuged at 9,000 rpm for 10 minutes, and the supernatant was used as the enzyme source of MDTS6. In this case, in addition to the expression plasmids described in Example 4 and Example 5, expression plasmids for three proteins, namely a protein in which the polypeptide represented by SEQ ID NO:33 was added to the C-terminus of the amino acids of from the 1st position to the 447th position of SEQ ID NO:1 (to be referred to as MDTS6Pro hereinafter), a protein in which the polypeptide represented by SEQ ID NO:33 was added to the C-terminus of the amino acids of from the 1st position to the 518th position of SEQ ID NO:1 (to be referred to as MDTS6Dis hereinafter) and a protein in which the polypeptide represented by SEQ ID NO:33 was added to the C-terminus of the amino acids of from the 1st position to the 687th position of SEQ ID NO:1 (to be referred to as MDTS6Cys hereinafter), were designed as expression plasmids for respective full-length MDTS6 proteins. That is, the MDTS6Cys expression plasmid was constructed by amplifying a gene by PCR using the full-length protein expression plasmid constructed in Example 5 as the template and the oligoDNA sequences represented by SEQ ID NO:7 and SEQ ID NO:17 as primers and using PyroBest DNA polymerase, digesting the gene with restriction enzymes XbaI and NotI, and then inserting the resulting fragment into the XbaI-NotI site of pCEP4dE2-FLAG. Also, the MDTS6Pro expression plasmid and the MDTS6Dis expression plasmid were constructed in the same manner as the plasmid prepared using the MDTS6Cys, illustratively, by digesting respective genes amplified by PCR using PyroBest DNA polymerase with restriction enzymes XbaI and NotI, and then inserting the resulting fragments into the XbaI-NotI site of pCEP4dE2-FLAG. Provided that the oligoDNA represented by SEQ ID NO:7 and the oligoDNA represented by SEQ ID NO:34 were used in the case of the MDTS6Pro, and a combination of the oligoDNA represented by SEQ ID NO:7 and the oligoDNA represented by SEQ ID NO:35 was used in the case of the MDTS6dis, respectively.

Regarding protein expression of these respective MDTS6 proteins (MDTS6Cys, MDTS6Pro and MDTS6Dis); they were expressed in the same manner as the expression of MDTS6TSP1 and MDTS6 full-length proteins in an animal cell strain described in (Example 6). When the aggrecanase activity of these respective MDTS6 proteins was examined by the method of Example 7-3, the aggrecanase activity was detected in the culture supernatant in which MDTS6Cys was expressed, but the aggrecanase activity was not detected in the culture supernatants in which MDTS6Pro and MDTS6Dis were expressed. In this connection, molecular weight of the expressed main protein was smaller than the value calculated from the amino acid sequence by a factor of about 23 K and, similar to the case of MDTS6TSP1 described in Example 6, it was mature protein in which the pro region was cleaved and removed at the furin protease recognition sequence. As a result, it was revealed that the first TSP-1 repeat sequence counting from the N-terminus is essential for exerting the aggrecanase activity of MDTS6.

EXAMPLE 9-2

Degradation of Natural Type Aggrecan

A 90 µl portion of the MDTS6 enzyme solution prepared in Example 9-1 was mixed with a solution of 10 µg natural type aggrecan (mfd. by Seikagaku Kogyo)/10 µl TBS in a test tube and allowed to undergo the reaction at 37° C. overnight. This reaction product was dried up using Speed-Vac and then dissolved in 100 µl of 10 mM Tris-acetate buffer (pH 7.6) containing 0.06 unit of Chondroitinase ABC (mfd. by Seikagaku Kogyo), 0.024 unit of keratanase I (mfd. by Seikagaku Kogyo), 0.0004 unit of keratanase II (mfd. by Seikagaku Kogyo), 5 µM of PMSF and 10 mM of EDTA, and the solution was allowed to undergo the reaction at 37° C. overnight. A portion of this reaction solution was subjected to SDS-PAGE and then the product was detected using the mouse anti-aggrecanase neoepitope antibody as shown in Example 7-3. In this case, the peroxidase-labeled goat anti-mouse IgG polyclonal antibody used was a preparation manufactured by Biosource. The same result was obtained by the BC-3 antibody which recognizes aggrecanase neoepitope (Hughes C. E. et al., Biochemical J., 305, 799–804, 1995).

Figure 5:
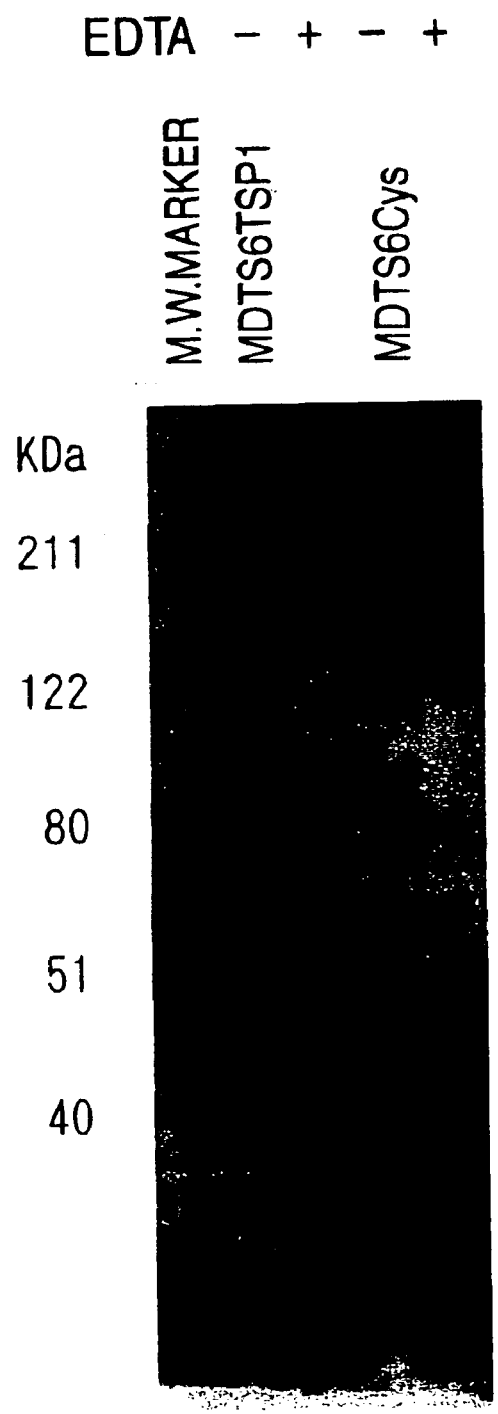
FIG. 5 is a photograph showing a result of the detection of degradation of natural type aggrecan by MDTS6 protein, by an anti-aggrecanase neoepitope antibody, using a western blotting detection system, obtained in Example 9-2.

As a result, a band of 80 to 90 KDa was detected in the case of MDTS6Cys in addition to a band of about 150 KDa. This degradation pattern is consistent with the pattern of main molecules (all generated by aggrecanase degradation) found in the joint synovial fluids of patients of joint diseases including OA and RA (Sandy J. D. et al., *J. Clin. Invest.*, 89, 1512–1516, 1992; Lohmander L. S. et al., *Arthritis Rheum.*, 36, 1214–1222, 1993) and also is consistent with the pattern of main molecules having aggrecanase neoepitope which are generated after 12 to 24 hours of treatment with IL-1 and retinoic acid in an explant culture system of human knee joint cartilage (Little C. B. et al., *Biochemical J.*, 344, 61–68, 1999) (FIG. 5).

EXAMPLE 10

Screening System of Substances which Modify the Aggrecanase Activity

EXAMPLE 10-1

Preparation of MDTS6Cys and Substrate

It was confirmed using the western blotting method shown in Example 9-2 that the recombinant aggrecan G1G2 and the natural type aggrecan are cleaved off at the site between $Glu^{373}$-$Ala^{374}$ (to be referred to as "aggrecanase site" hereinafter) by MDTS6Cys without purification but as the culture supernatant prepared by the method of Example 9-1. Also, the cleavage at the "aggrecanase site" was observed when the culturing in Example 9-1 was continued with the 10% FBS-containing medium without changing to the serum-free medium. Accordingly, the recombinant aggrecan G1G2 prepared in Example 7-1 was used as the substrate.

EXAMPLE 10-2

Screening System

Though the screening can be carried out by the western blotting-aided method shown in Example 7-2 using the recombinant aggrecan or natural type aggrecan as the substrate, the following ELISA system was constructed for screening more larger number of compounds to be tested.

An MDTS6Cys culture supernatant, the recombinant aggrecan G1G2 and a compound to be tested were mixed and allowed to undergo the reaction at 37° C. for several hours, the resulting product was adhered to a 96 well plate (Nunc-Immuno™ Plate MaxiSorp™ Surface #439454; mfd. by Nunc), blocked with 1% BSA/TBS solution and then allowed to react with a mouse anti-aggrecanase neoepitope antibody and an HRP-anti-mouse IgG antibody conjugate (mfd. by Biosource) in that order, and then the detection was carried out using TMB Peroxidase EIA Substrate Kit (mfd. by Bio-Rad) under the conditions described in the attached instructions to calculate the aggrecanase activity inhibiting strength of the compound to be tested using the coloring inhibition as a marker. Also, as a modified method thereof, the recombinant aggrecan was adhered to the 96 well plate (mfd. by Nunc) and blocked with 1% BSA/TBS solution in advance and then an MDTS6Cys culture supernatant and a compound to be tested were added thereto and allowed to undergo the reaction at 37° C. for several hours, the resulting product was allowed to react with a mouse anti-aggrecanase neoepitope antibody and an HRP-anti-mouse IgG antibody conjugate (mfd. by Biosource) in that order, and then the detection was carried out using TMB Peroxidase EIA Substrate Kit (mfd. by Bio-Rad) to calculate the aggrecanase activity inhibiting strength of the compound to be tested using the coloring inhibition as a marker. The criterion to screen a substance which inhibits the aggrecanase activity is preferably 10 µM or less, more preferably 1.0 µM or less, as inhibition activity strength ($IC_{50}$)

By this screening system, it was able to select the aforementioned compound A, compound B, compound C and compound D. The aggrecanase activity inhibition strength ($IC_{50}$) was 0.6 µM for the compound A, 1.0 µM for the compound B, 2.9 µM for the compound C and 2.7 µM for the compound D.

In this connection, the compound A, compound B, compound C and compound D were synthesized in the same manner as the production method described in PCT publication number WO 90/05719. The mass spectrum of respective compounds is as follows. The compound A is MS=426 ($MH^+$), the compound B is MS=396 ($MH^+$), the compound C is MS=502 ($MH^+$) and the compound D is MS=440 ($MH^+$)

EXAMPLE 11

EXAMPLE 11-1

Preparation of Rabbit Knee Joint Cartilage Primary Culture Cells

After killing a rabbit (Japanese white species, male, 1.0 to 1.5 kg) under excess anesthesia, a knee joint was excised and the cartilage layer on the joint surface was removed and finely cut using a surgical knife. The cut pieces were treated with trypsin-EDTA (0.25%-1 mM; mfd. by GIBCO-BRL) at 37° C. for 1 hour and then centrifuged at 1,500 rpm for 5 minutes, and the resulting precipitate was washed with DMEM. This was treated with collagenase A (0.15%; Boehringer-Mannheim)/DMEM at 37° C. for 3 to 4 hours, and then a nylon mesh filter (100 µm, mfd. by Falcon)-passed fraction was centrifuged at 1,500 rpm for 5 minutes to effect precipitation of cartilage cells. The cells were thoroughly washed with DMEM/10% FBS medium, suspended in DMEM/10% FBS medium to a density of $2 \times 10^5$ cells/ml and then inoculated in 200 µl/well portions into an I type collagen-coated 96 well plate (mfd. by Asahi Technoglass). Three days thereafter, the medium was changed to 200 µof DMEM/10% FBS medium containing 50 µg/ml of ascorbic acid (ascorbic acid medium hereinafter), and the culturing was continued for 3 days. When an I type collagen-coated 6 well plate (Asahi Technoglass) was used, the cell suspension was inoculated in 6 ml/well portions and cultured by carrying out the same medium exchange. These cells were used in the following test.

EXAMPLE 11-2

Figure 6:
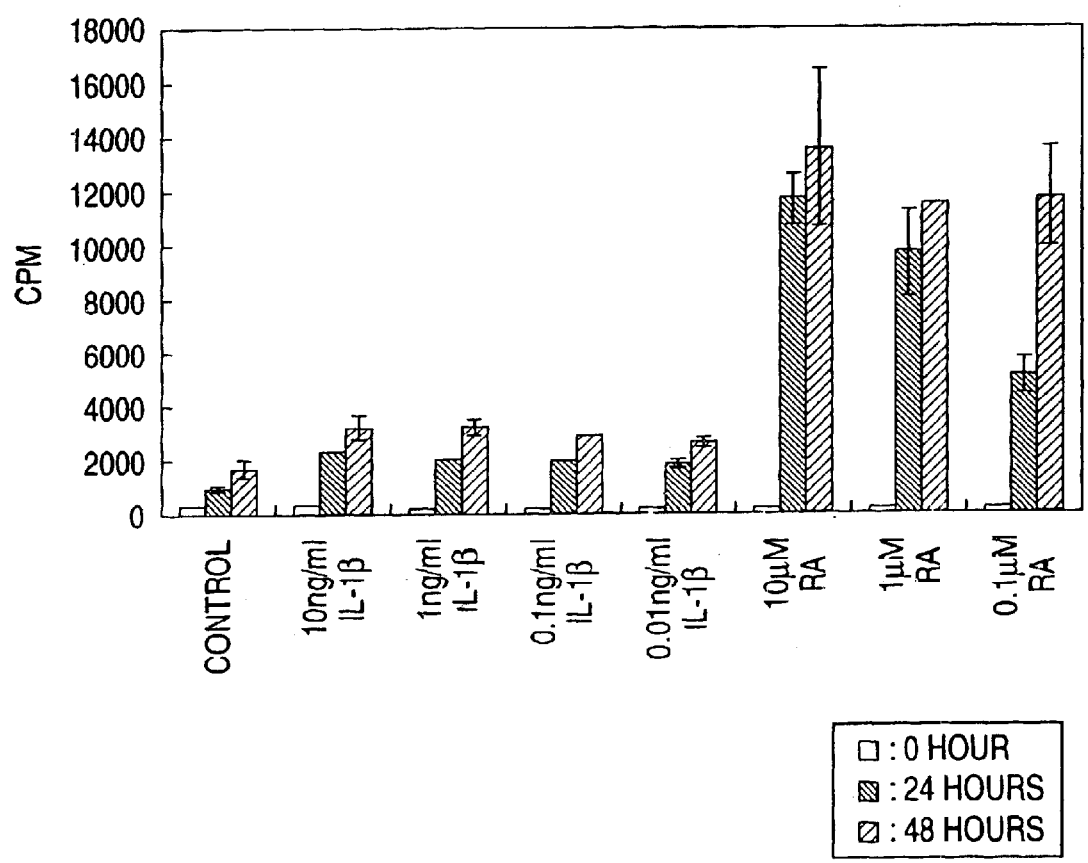
FIG. 6 is a graph showing a result of the detection of release of proteoglycan from rabbit knee joint primary culture cells by all-trans retinoic acid and IL-1β, obtained in Example 11-2.

Proteoglycan Degradation of Rabbit Knee Joint Cartilage Primary Culture Cells The rabbit knee joint cartilage primary culture cells of 96 well plate described in Example 11-1 were cultured for 2 days using 200 µl of the ascorbic acid medium supplemented with 10 µCi/ml in final concentration of $Na_2{}^{35}SO_4$ and labeled therewith, washed 3 times with 200 µl of the ascorbic acid medium and then cultured for 1 day using 200 µl of the ascorbic acid medium. After stimulation with IL-1β or all-trans retinoic acid and subsequent 0, 24, and 48 hours of culturing, the culture supernatants were recovered in 20 µl portions, and the radioactivity was measured using Top Count (mfd. by Packard). As a result, increase in the radioactivity, namely release of proteoglycan, was observed by 0.01 to 10 ng/ml of IL-1β stimulation, and increase in the concentration-dependent and strong radioactivity, namely release of proteoglycan, was observed by 0.1 to 10 µM of all-trans retinoic acid stimulation (FIG. 6).

EXAMPLE 11-3

Induction of MDTS6 mRNA Expression

Figure 7:
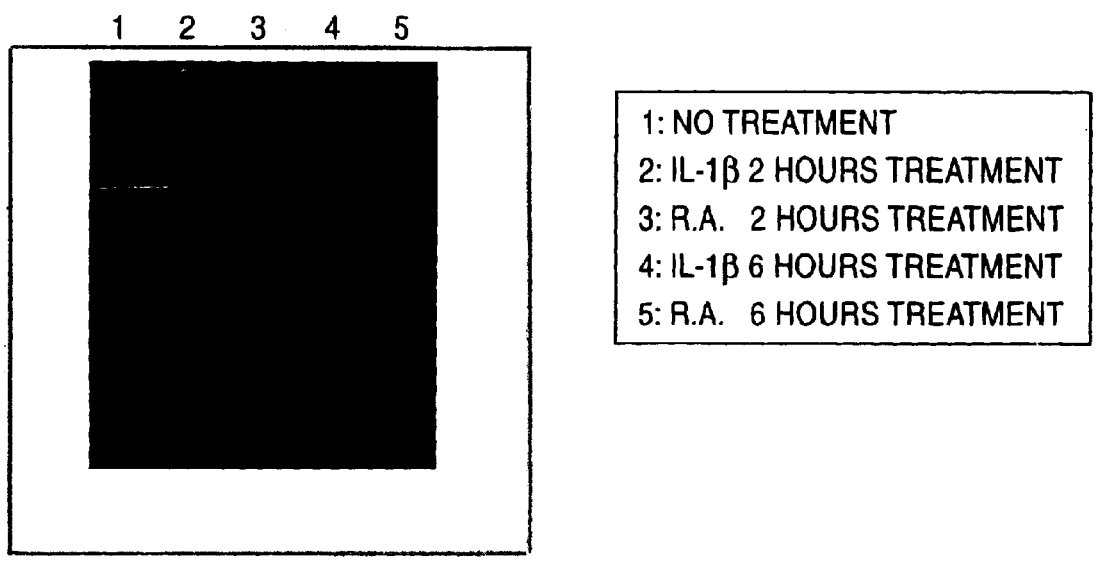
FIG. 7 is an electrophoresis pattern photograph showing a result of the analysis of changes in gene expression of MDTS6 by RT-PCR when rabbit knee joint primary culture cells are treated with all-trans retinoic acid and IL-1β, obtained in Example 11-3.

After 3 days of culturing of the rabbit knee joint cartilage primary culture cells of 6 well plate described in Example 11-1 by changing the medium to ascorbic acid medium, 10 ng/ml of IL-1β or 10 µM of all-trans retinoic acid was added thereto, and total RNA samples 2 and 6 hours thereafter were prepared using ISOGEN (mfd. by Nippon Gene) in accordance with the attached instructions. Each of the samples was treated with DNase I (mfd. by Nippon Gene), subjected to phenol/chloroform treatment and then recovered by ethanol precipitation, and the thus purified total RNA was dissolved in DEPC-treated sterile water. Using random hexamers as primers, 1 µg of this total RNA was subjected to reverse transcription reaction and RNase H treatment using Thermoscript™ RT-PCR System (mfd. by GIBCO-BRL, catalog number 11146-016) in accordance with the attached instructions, and the product was diluted 10 times with sterile water and used as a cDNA sample. Using 5 µl of each of the thus obtained cDNA samples as the template and the oligoDNA sequences represented by SEQ ID NO:18 and SEQ ID NO:19 as primers, PCR was carried out under a condition of 94° C. for 2 minutes, 45 repetitions of a cycle of 94° C. for 30 seconds, 65° C. for 30 seconds and 72° C. for 30 seconds, and subsequent 72° C. for 10 minutes. The reaction products were subjected to 2% agarose electrophoresis, and densities of the generated DNA fragments were compared. As a result, expression of the MDTS6 mRNA was induced by IL-1β and all-trans retinoic acid, and the expression strength correlated with the degree of proteoglycan degradation described in Example 11-2 (FIG. 7).

EXAMPLE 12

Figure 8:
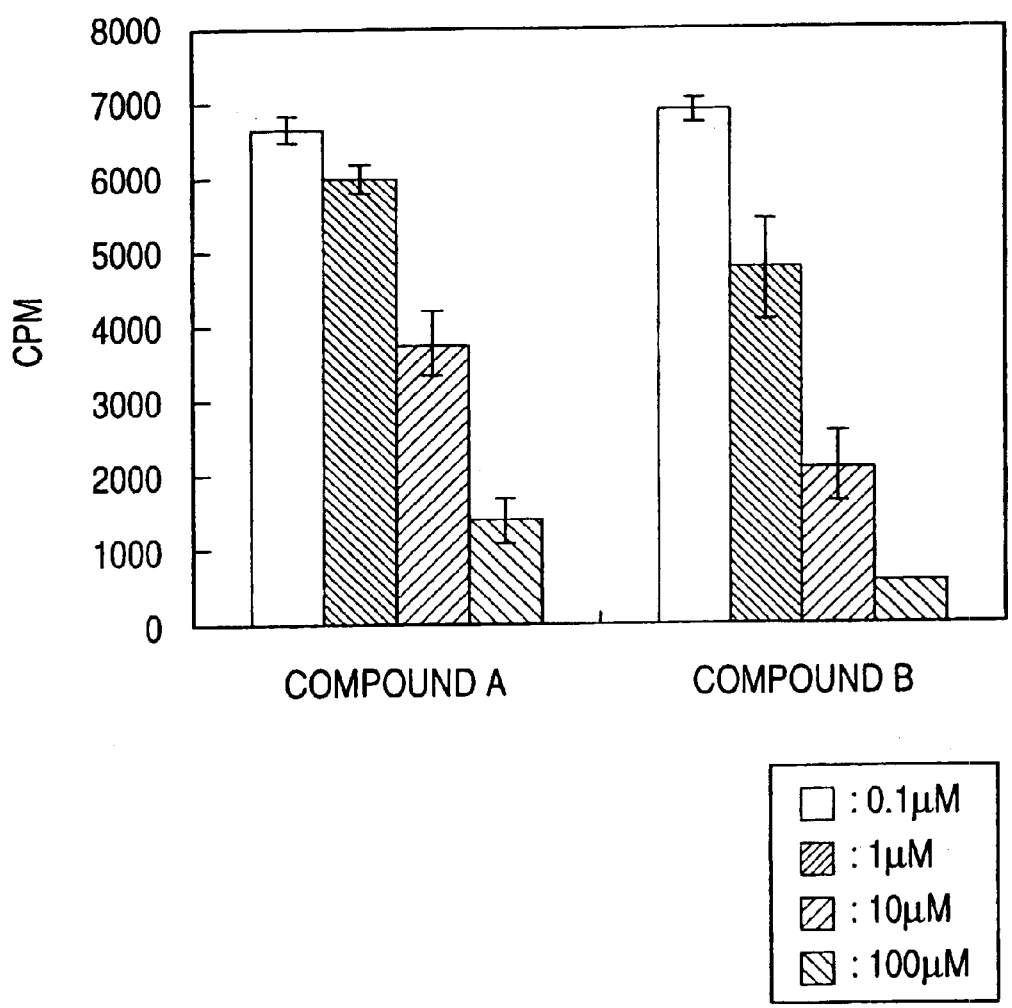
FIG. 8 is a graph showing that degradation and release of proteoglycan from rabbit knee joint primary culture cells by all-trans retinoic acid are inhibited by the compound A and compound B, obtained in Example 12.

Inhibition of Proteoglycan Degradation in Rabbit Knee Joint Cartilage Primary Culture Cells by Substances which Inhibit the Aggrecanase Activity Each of the compounds A, B, C and D selected by the screening system of Example 10-2 was added to the proteoglycan degradation system of rabbit knee joint cartilage primary culture cells just before the stimulation with 10 µM of all-trans retinoic acid, and their proteoglycan degradation inhibitory activities were examined. As a result, the compounds A and B showed the inhibition of proteoglycan degradation in a concentration-dependent manner (FIG. 8). The proteoglycan degradation inhibition action ($IC_{50}$) of the compounds C and D was 6.3 µM for the compound C and 4.1 µM for the compound D. On the other hand, the proteoglycan degradation inhibition action was not observed by compounds which have the same hydroxamic acid backbone but show a weak aggrecanase activity inhibition, even at a concentration of 100 µM.

EXAMPLE 13

Analysis of MDTS6 Promoter Region DNA Sequence

A DNA fragment corresponding to the promoter region of MDTS6 was amplified using PCR from GenomeWalker DNA Sca I Libraries (Genome Walkers™ Kits, CLONTECH catalog number K1803-1). OligoDNA sequences of the adapter primers AP-1 (SEQ ID NO:20) and AP-2 (SEQ ID NO:21) attached to the kit were used as forward primers, and the oligoDNA sequences of SEQ ID NO:22 and SEQ ID NO:23 as reverse primers. The illustrative method was as described in the instructions attached to the kit, but TAKARA LA Taq (TAKRRA LA Taq™, catalog number RR002A) was used in the PCR. The first PCR was carried out using the oligoDNA sequences of SEQ ID NO:20 and SEQ ID NO:22 as primers under a condition of 7 repetitions of a cycle of 98° C. for 5 seconds and 72° C. for 3 minutes, 32 repetitions of a cycle of 98° C. for 5 seconds and 67° C. for 3 minutes, and 67° C. for 4 minutes. The second PCR was carried out under the same conditions using 5 µl of a solution prepared by diluting the reaction solution of the first reaction 50 times with TE buffer (10 mM Tris-HCl, 1 mM EDTA, pH 8.0) as the template, and the oligoDNA sequences of SEQ ID NO:21 and SEQ ID NO:23 as primers. When the thus amplified DNA fragment of about 3.7 kbp was directly subjected to sequence analysis by dideoxy terminator method using ABI377 DNA Sequencer (Applied Biosystems Inc.), DNA sequences of about 2.2 kbp, 0.36 kbp and 0.8 kbp divided by two un-decipherable gaps were found.

Next, in order to decipher sequences of these two gap moieties which were unable to decipher by the direct analysis of the PCR-amplified DNA fragment, this DNA fragment was subcloned and the DNA nucleotide sequence was determined. As a result, sequences of the gap moieties were different in the determined 8 clones (SEQ ID NOs:24, 25, 26, 27, 28, 29, 30 and 31), so that the presence of gene polymorphism was suggested. In this connection, pZErO™-2 vector (Zero Background/Kan Cloning Kit, mfd. by Invitrogen, catalog number K2600-01) was used as the cloning vector, and the subcloning was carried out in accordance with the attached instructions.

A plasmid prepared by inserting the above DNA fragment into the KpnI-XhoI site of a reporter plasmid pGV-B 2 (mfd. by Toyo Ink) was introduced into HEK293 cell using FuGene-6, and the luciferase activity after 28 or 48 hours of culturing under usual culturing conditions was measured using PicaGene coloring kit (mfd. by Toyo Ink, catalog number PGK-L100). In this case, the measured value was normalized by the activity value of β-gal expressed by a simultaneously introduced β-gal expression plasmid pCH110 (Amersham Pharmacia Biotech, catalog number 27-4508-01). The β-gal activity was measured using Galacto-Light Plus Kit (mfd. by TROPIX, catalog number BL300P). As a result, distinct increase in the luciferase activity which cannot be found in the original plasmid pGV-B2 was observed. This result indicates that the promoter activity is present in the above DNA fragment.

EXAMPLE 14

Expression of MDTS6 in Joint Tissue of Osteoarthritis Patient

Total RNA was prepared from an affected part of a knee joint cartilage of an osteoarthritis patient (Adams M. E. et al., *Anal. Biochem.*, 202, 89–95, 1992), and the presence of MDTSG mRNA was confirmed by carrying out RT-PCR using this as the template in accordance with Example 11-3. Also, the presence of MDTS6 protein in synovial membrane and macrophage was confirmed by carrying out immunological tissue staining using a mouse anti-human MDTS6-specific polyclonal antibody.

In this connection, the mouse anti-human MDTS6-specific polyclonal antibody was prepared in the following manner. Firstly, the MDTS6TSP1 protein prepared in Example 6 was conjugated with KLH, and mice were immunized with this 4 to 5 times to obtain an antiserum sample. Next, IgG was prepared from this antiserum using Protein G Sepharose 4 Fast Flow (mfd. by Amersham Pharmacia Biotech) in accordance with the attached instructions. Next, a column in which the human MDTS6TSP1 protein was fixed to CNBr-activated Sepharose 4 Fast Flow (mfd. by Amersham Pharmacia Biotech) was prepared in accordance with the attached instructions. Thereafter, a fraction was prepared which binds to this column but does not bind to a column immobilized with human ADAMTS4TSP1 protein (aggrecanase-1; Tortorella M. D. et al., *Science*, 284, 1664–1666, 1999), METH-1TSP1 protein (Vazquez F. et al., *J. Biol. Chem.*, 274, 23349–57, 1999) or METH-2TSP1 protein (Vazquez F. et al., *J. Biol. Chem.*, 274, 23349–57, 1999).

Industrial Applicability

The "joint disease aggrecanase" obtained by the invention is characterized in that it can be used for the screening of a substance which significantly inhibits the aggrecanase (a compound, a peptide, an antibody or an antibody fragment), because it has an aggrecanase activity. Regarding the medicinal use of the substance which significantly inhibits the "joint disease aggrecanase", it is suggested that it is effective in preventing and treating diseases which are caused by abnormalities (e.g., acceleration, reduction, degeneration and the like) of the aggrecanase activity or in which the abnormalities are expressed to cause complications, particularly joint diseases as diseases which show acceleration of proteoglycan degradation, most particularly osteoarthritis.

Also, the promoter gene of the "joint disease aggrecanase" of the invention is characterized in that it can be used for the screening of a substance which inhibits promoter activity of the gene (a compound, a peptide, an antibody or an antibody fragment). As the use of the substance which inhibits the promoter activity, it is suggested that it is effective in preventing and treating diseases caused by inhibition of the promoter activity, particularly joint diseases as diseases which show acceleration of proteoglycan degradation, most particularly osteoarthritis. In addition, since two or more mutants are present in the promoter gene, they can be used for their correlation analysis with these diseases.

---

What is claimed is:

1. A purified metalloprotease comprising an amino acid sequence represented by amino acids 213–583 of SEQ ID NO:1 or an amino acid sequence represented by amino acids 213–583 of SEQ ID NO:1 wherein from 1 to 10 amino acid residues are substituted, deleted and/or inserted, and wherein said metalloprotease has aggrecanase activity.

2. A purified metalloprotease comprising an amino acid sequence represented by amino acids 1–583 of SEQ ID NO:1 or an amino acid sequence represented by amino acids 1–583 of SEQ ID NO:1 wherein from 1 to 10 amino acid residues are substituted, deleted and/or inserted, and wherein said metalloprotease has aggrecanase activity.

3. A purified metalloprotease comprising an amino acid sequence selected from the group consisting of an amino acid sequence represented by amino acids 1–950 of SEQ ID NO:1, an amino acid sequence represented by amino acids 1–687 of SEQ ID NO:1, an amino acid sequence represented by amino acids 1–583 of SEQ ID NO:1, an amino acid sequence represented by amino acids 213–950 of SEQ ID NO:1, an amino acid sequence represented by amino acids 213–687 of SEQ ID NO:1, an amino acid sequence represented by amino acids 213–583 of SEQ ID NO:1, and any one of said sequences wherein from 1 to 10 amino acid residues are substituted, deleted and/or inserted, and wherein said metalloprotease has aggrecanase activity.

4. A purified metalloprotease comprising an amino acid sequence which has 90% or more sequence homology with the amino acid sequence set forth in SEQ ID NO:1, wherein said metalloprotease has aggrecanase activity.

5. An isolated polynucleotide which encodes a metalloprotease having aggrecanase activity of any one of claims 1–4.

6. A cloning or expression vector comprising the polynucleotide of claim 5.

7. A host cell transformed with the vector of claim 6.

8. A method for producing a metalloprotease having aggrecanase activity and comprising an amino acid sequence represented by amino acids 213–583 of SEQ ID NO:1 or an amino acid sequence represented by amino acids 213–583 of SEQ ID NO:1 wherein from 1 to 10 amino acid residues are substituted, deleted and/or inserted, said method comprising a) culturing the host cell of claim 7 under conditions such that said host cell expresses said metalloprotease, and b) recovering the metalloprotease so expressed.

9. A method for producing a metalloprotease having aggrecanase activity and comprising an amino acid sequence represented by amino acids 1–583 of SEQ ID NO:1 or an amino acid sequence represented by amino acids 1–583 of SEQ ID NO:1 wherein from 1 to 10 amino acid residues are substituted, deleted and/or inserted, said method comprising a) culturing the host cell of claim 7 under conditions such that said host cell expresses said metalloprotease, and b) recovering the metalloprotease so expressed.

10. A method for producing a metalloprotease having aggrecanase activity and comprising an amino acid sequence selected from the group consisting of an amino acid sequence represented by amino acids 1–950 of SEQ ID NO:1, an amino acid sequence represented by amino acids 1–687 of SEQ ID NO:1, an amino acid sequence represented by amino acids 1–583 of SEQ ID NO:1, an amino acid sequence represented by amino acids 213–950 of SEQ ID NO:1, an amino acid sequence represented by amino acids 213–687 of SEQ ID NO:1, an amino acid sequence represented by amino acids 213–583 of SEQ ID NO:1 and any one of these sequences wherein from 1 to 10 amino acid residues are substituted, deleted and/or inserted, said method comprising a) culturing the host cell of claim 7 under conditions such that said host cell expresses said metalloprotease, and b) recovering the metalloprotease so expressed.

* * * * *